US012564553B2

(12) United States Patent (10) Patent No.: US 12,564,553 B2

Yamashita (45) Date of Patent: *Mar. 3, 2026

(54) SUSPENSION CONTAINING HETEROCYCLIDENE ACETAMIDE DERIVATIVE

(71) Applicants: SENJU PHARMACEUTICAL CO., LTD., Osaka (JP); MOCHIDA PHARMACEUTICAL CO., LTD., Tokyo (JP)

(72) Inventor: Yuki Yamashita, Osaka (JP)

(73) Assignees: SENJU PHARMACEUTICAL CO., LTD., Osaka (JP); MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/553,141

(22) PCT Filed: Mar. 29, 2022

(86) PCT No.: PCT/JP2022/015691

§ 371 (c)(1),
(2) Date: Sep. 28, 2023

(87) PCT Pub. No.: WO2022/210784

PCT Pub. Date: Oct. 6, 2022

(65) Prior Publication Data

US 2024/0180827 A1     Jun. 6, 2024

(30) Foreign Application Priority Data

Mar. 30, 2021    (JP) ................................. 2021-057713

(51) Int. Cl.
| *A61K 9/10* | (2006.01) |
| *A61K 9/00* | (2006.01) |
| *A61K 31/353* | (2006.01) |
| *A61K 47/02* | (2006.01) |
| *A61K 47/10* | (2017.01) |
| *A61K 47/26* | (2006.01) |
| *A61K 47/38* | (2006.01) |
| *A61K 47/44* | (2017.01) |

(52) U.S. Cl.
CPC .............. *A61K 9/10* (2013.01); *A61K 9/0048* (2013.01); *A61K 31/353* (2013.01); *A61K 47/02* (2013.01); *A61K 47/10* (2013.01); *A61K 47/26* (2013.01); *A61K 47/38* (2013.01); *A61K 47/44* (2013.01)

(58) Field of Classification Search
None
See application file for complete search history.

(56) References Cited

U.S. PATENT DOCUMENTS

| 5,652,272 | A | 7/1997 | Ogawa et al. |
| 2001/0036966 | A1* | 11/2001 | Yasueda ................... A61K 9/08 |
| | | | 514/772.7 |
| 2003/0008010 | A1 | 1/2003 | Yasueda et al. |
| 2008/0287428 | A1 | 11/2008 | Uchida et al. |
| 2009/0312724 | A1* | 12/2009 | Pipkin ................. A61K 31/724 |
| | | | 128/207.18 |
| 2011/0112071 | A1 | 5/2011 | Uchida et al. |
| 2018/0346436 | A1* | 12/2018 | Satoh ........................ A61P 1/04 |
| 2022/0370404 | A1 | 11/2022 | Tarui et al. |

FOREIGN PATENT DOCUMENTS

| EP | 1908753 A1 | 4/2008 |
| JP | H07-304663 A | 11/1995 |
| JP | H11-029463 A | 2/1999 |
| WO | 2007/010383 A1 | 1/2007 |
| WO | 2008/123396 A1 | 10/2008 |
| WO | 2018/221543 A1 | 12/2018 |
| WO | 2021/039748 A1 | 3/2021 |
| WO | 2021/066144 A1 | 4/2021 |

OTHER PUBLICATIONS

Banshoya et al., "Coenzyme Q10-Polyethylene Glycol Monostearate Nanoparticles: An Injectable Water-Soluble Formulation," Antioxidants, 9(1): 86 (2020).

Barrios et al., "Salt-Induced Diffusiophoresis of a Nonionic Micelle: Roles of Salting Out and Proximity to Surfactant Cloud Point," Journal of Molecular Liquids, 359: 119271 (2022).

BASF, "Cremophor® RH 60," Technical Information Document PRD 30035153 (2020).

Lee et al., "Equilibrium and Dynamic Interfacial Tension Measurements at Microscopic Interfaces Using a Micropipet Technique. 1. A New Method for Determination of Interfacial Tension," Langmuir, 17(18): 5537-5543 (2001).

Pogorzelski et al., "Surface Tensometry Studies on Formulations of Surfactants with Preservatives as a Tool for Antimicrobial Drug Protection Characterization," Journal of Biophysical Chemistry, 3(4): 324-333 (2012).

Saito et al., "Micellar Formation and Micellar Structure of Poly(oxyethylene)-hydrogenated Castor Oil," Yakugaku Zasshi, 112(10): 763-767 (1992).

Salager, "Surfactants in Aqueous Solutions," FIRP Booklet # E201-A (1994).

Nagai, "Evaluation Based on Pharmaceutical Characteristics and Design of Novel Nanomedicine in the Ophthalmic Field," Iryo Yakugaku (Japanese Journal of Pharmaceutical Heath Care and Sciences), 44(10): 481-490 (2018).

Onda, "Synthesis and Properties of Cellulose Derivatives as Pharmaceutical Additives," Journal of the Society of Synthetic Organic Chemistry, 42(6): 602-606 (1984).

(Continued)

*Primary Examiner* — Melissa S Mercier

(74) *Attorney, Agent, or Firm* — Leydig, Voit & Mayer, Ltd.

(57) ABSTRACT

The present disclosure provides suspendable ophthalmic solutions with excellent redispersibility. The present disclosure provides an aqueous suspension agent comprising (E)-2-(7-trifluoromethylchroman-4-ylidene)-N-(7-hydroxy-5,6,7,8-tetrahydronaphthalen-1-yl)acetamide       or       a pharmaceutically acceptable salt or solvate thereof, a cellulosic polymer, and a nonionic surfactant.

9 Claims, 1 Drawing Sheet

(56)  References Cited

OTHER PUBLICATIONS

European Patent Office, Extended European Search Report in European Patent Application No. 22780995.1 (Feb. 24, 2025).
Japan Patent Office, International Search Report in International Patent Application No. PCT/JP2022/015691 (May 24, 2022).
Japan Patent Office, Office Action in Japanese Patent Application No. 2022-546133 (Oct. 12, 2022).
Japan Patent Office, Office Action in Japanese Patent Application No. 2022-178888 (Feb. 24, 2023).

* cited by examiner

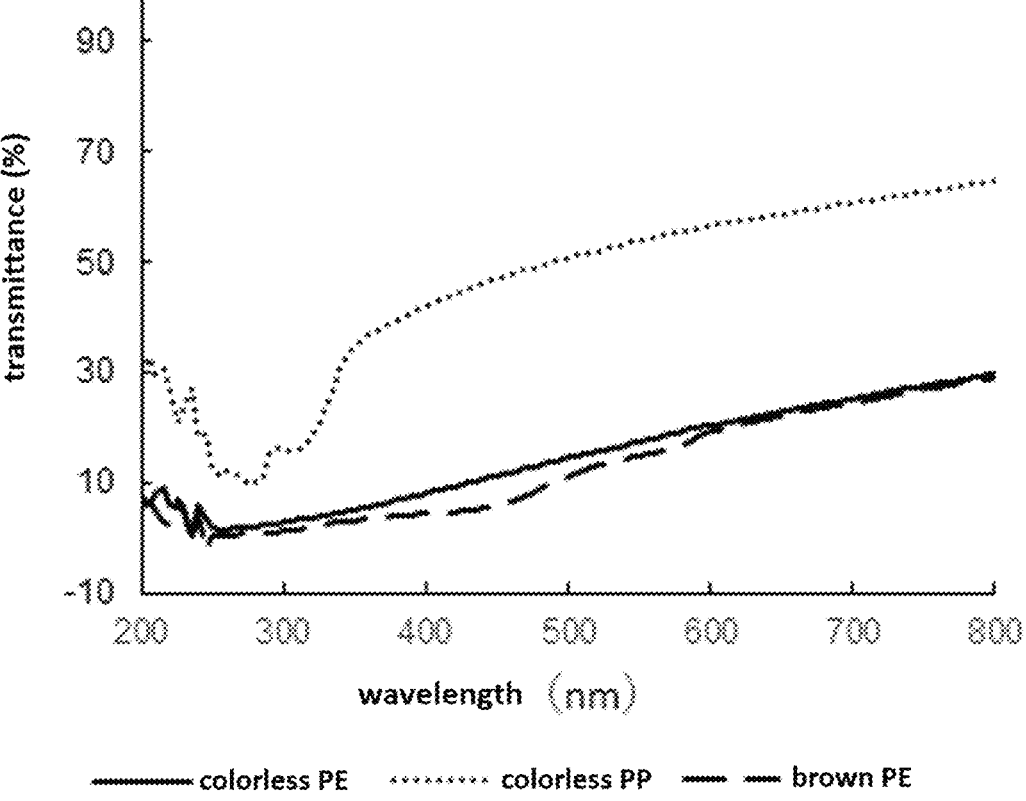

SUSPENSION CONTAINING HETEROCYCLIDENE ACETAMIDE DERIVATIVE

TECHNICAL FIELD

The present disclosure relates to fields such as medicine, healthcare, biology and biotechnology. The present disclosure relates, inter alia, to techniques for improving the redispersibility of suspensions containing heterocyclideneacetamide derivatives, and formulation techniques based thereon.

BACKGROUND ART

The population of dry eye patients in Japan is estimated to be at least about 8 million, and about 22 million including potential patients who use over-the-counter eye drops without going to the hospital. It is said that there are more than 1 billion dry eye patients in the world. In modern society, the use of televisions, computers, mobile terminals, etc., increases the number of times we stare at the screen and the number of times we blink decreases. Furthermore, it is widely known that the use of an air conditioner or the like dries the air, resulting in accelerated tear evaporation and dry eye. In addition, refractive surgery and contact lens use result in dry eyes. Symptoms associated with dry eye include ocular discomfort, dryness, burning and irritation of the ocular surface.

When dry eye develops, the above symptoms appear as subjective symptoms, and treatment thereof requires regular eye drops over a long period of time. Therefore, most dry eye therapeutic agents currently on the market, in general, are in the form of frequent administration. For example, Diquas ophthalmic solution should be applied 6 times a day, hyaline ophthalmic solution should be applied 5 to 6 times a day, and Mucosta ophthalmic solution should be applied 4 times a day.

SUMMARY OF INVENTION

Solution to Problem

The present disclosure provides an aqueous suspension agent with excellent redispersibility, the aqueous suspension agent comprising: (E)-2-(7-trifluoromethylchroman-4-ylidene)-N-(7-hydroxy-5,6,7,8-tetrahydronaphthalen-1-yl) acetamide, which is one of the heterocyclideneacetamide derivatives; or a pharmaceutically acceptable salt or solvate thereof.

The present disclosure thus provides the following:
(Item 1)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a cellulosic polymer; and a nonionic surfactant.
(Item 2)

The aqueous suspension agent of the preceding item, wherein the concentration of the cellulosic polymer in the aqueous suspension agent is from about 0.00007 w/v % to about 0.01 w/v %.
(Item 2a)

The aqueous suspension agent of the preceding items, wherein the concentration of the cellulosic polymer in the aqueous suspension agent is from about 0.00007 w/v % to about 0.007 w/v %.

(Item 3)

The aqueous suspension agent of any one of the preceding items, wherein the concentration of the cellulosic polymer in the aqueous suspension agent is from about 0.0001 w/v % to about 0.008 w/v %.
(Item 3a)

The aqueous suspension agent of any one of the preceding items, wherein the concentration of the cellulosic polymer in the aqueous suspension agent is from about 0.0001 w/v % to about 0.005 w/v %.
(Item 4)

The aqueous suspension agent of any one of the preceding items, wherein the cellulosic polymer is at least one selected from the group consisting of methylcellulose, hydroxypropylmethylcellulose, and carboxymethylcellulose.
(Item 5)

The aqueous suspension agent of any one of the preceding items, wherein the concentration of the nonionic surfactant in the aqueous suspension is from about 0.0001 w/v % to about 0.5 w/v %.
(Item 6)

The aqueous suspension agent of any one of the preceding items, wherein the concentration of the nonionic surfactant in the aqueous suspension is from about 0.0001 w/v % to about 0.1 w/v %.
(Item 6a)

The aqueous suspension agent of any one of the preceding items, wherein the concentration of the nonionic surfactant in the aqueous suspension is from about 0.01 w/v % to about 0.05 w/v %.
(Item 7)

The aqueous suspension agent of any one of the preceding items, wherein the nonionic surfactant is at least one selected from the group consisting of tyloxapol, polysorbate 80, polyethylene glycol monostearate, and polyoxyethylene hydrogenated castor oil.
(Item 8)

The aqueous suspension agent of any one of the preceding items, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof in the aqueous suspension is from about 0.01% w/v to about 5% w/v.
(Item 9)

The aqueous suspension agent of any one of the preceding items, further comprising a zinc salt or a silver salt.
(Item 10)

The aqueous suspension agent of any one of the preceding items, wherein the concentration of the zinc salt or silver salt in the aqueous suspension is from about 0.0001 w/v % to about 0.05 w/v %.
(Item 11)

The aqueous suspension agent of any one of the preceding items, wherein the zinc salt is zinc chloride or zinc sulfate.
(Item 11a)

The aqueous suspension agent of any one of the preceding items, wherein the silver salt is silver nitrate.
(Item 12)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide is (E)-2-(7-trifluoromethylchroman-4-ylidene)-N-((7R)-7-hydroxy-5,6,7,8-tetrahydronaphthalen-1-yl) acetamide.
(Item 13)

The aqueous suspension agent of any one of the preceding items, further comprising a borate buffer.

(Item 14)

The aqueous suspension agent of any one of the preceding items, wherein the aqueous suspension has a pH of about 4 to about 8.

(Item 15)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved redispersibility.

(Item 16)

The aqueous suspension agent of any one of the preceding items, wherein the improvement in redispersibility is the redispersion of suspended particles at about 15 or fewer shakes, when evaluated by a shaking operation.

(Item 17)

The aqueous suspension agent of any one of the preceding items, wherein the improvement in redispersibility is the redispersion of suspended particles at about 40 or fewer inversions when evaluated by an inversion operation.

(Item 18)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved stability.

(Item 19)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved redispersibility, and wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved stability.

(Item 20)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has an average particle size of about 1 μm to about 5 μm.

(Item 21)

The aqueous suspension agent of any one of the preceding items, wherein the aqueous suspension agent is contained in a plastic container.

(Item 22)

The aqueous suspension agent of any one of the preceding items, wherein the material of the plastic container is polyethylene or polypropylene.

(Item 23)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a cellulosic polymer; and a nonionic surfactant, wherein the concentration of the cellulosic polymer in the aqueous suspension agent is from about 0.0001 w/v % to about 0.005 w/v %, wherein the cellulosic polymer is at least one selected from the group consisting of methylcellulose, hydroxypropylmethylcellulose, and carboxymethylcellulose, wherein the concentration of the nonionic surfactant in the aqueous suspension is from about 0.01 w/v % to about 0.05 w/v %, wherein the nonionic surfactant is at least one selected from the group consisting of tyloxapol, polysorbate 80, and polyethylene glycol monostearate, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item 24)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a cellulosic polymer; and a nonionic surfactant, wherein the concentration of the cellulosic polymer in the aqueous suspension agent is from about 0.0001 w/v % to about 0.005 w/v %, wherein the cellulosic polymer is at least one selected from the group consisting of methylcellulose, hydroxypropylmethylcellulose, and carboxymethylcellulose, wherein the concentration of the nonionic surfactant in the aqueous suspension is from about 0.01 w/v % to about 0.05 w/v %, wherein the nonionic surfactant is at least one selected from the group consisting of tyloxapol, polysorbate 80, and polyethylene glycol monostearate, the aqueous suspension agent further comprising a zinc salt or silver salt, and a borate buffer, wherein the zinc salt or silver salt is at least one selected from the group consisting of zinc chloride, zinc sulfate and silver nitrate, wherein the concentration of the zinc salt or silver salt in the aqueous suspension is from about 0.0005% w/v to about 0.01% w/v, wherein the aqueous suspension has a pH of about 4 to about 8, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item 25)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a cellulosic polymer; and a nonionic surfactant, wherein the concentration of the cellulosic polymer in the aqueous suspension agent is from about 0.0001 w/v % to about 0.005 w/v %, wherein the cellulosic polymer is methylcellulose, wherein the concentration of the nonionic surfactant in the aqueous suspension is from about 0.01 w/v % to about 0.05 w/v %, wherein the nonionic surfactant is tyloxapol, the aqueous suspension agent further comprising zinc chloride and a borate buffer, wherein the concentration of the zinc chloride in the aqueous suspension is from about 0.0005% w/v to about 0.01% w/v, wherein the aqueous suspension has a pH of about 4 to about 8, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item 26)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a cellulosic polymer; and a nonionic surfactant, wherein the concentration of the cellulosic polymer in the aqueous suspension agent is from about 0.0005 w/v % to about 0.003 w/v %, wherein the cellulosic polymer is methylcellulose, wherein the concentration of the nonionic surfactant in the aqueous suspension is from about 0.01 w/v % to about 0.03 w/v %, wherein the nonionic surfactant is tyloxapol, the aqueous suspension agent further comprising a borate buffer, wherein the aqueous suspension has a pH of about 6.0 to about 8.0, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.3% w/v to about 1.0% w/v, and wherein the (E)-2-(7-trifluoromethylchroman-4-ylidene)-N-(7-hydroxy-5,6,7,8-tetrahydronaphthalen-1-yl)acetamide is (E)-2-(7-trifluoromethylchroman-4-ylidene)-N-((7R)-7-hydroxy-5,6,7,8-tetrahydronaphthalen-1-yl)acetamide.

(Item 27)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a cellulosic polymer; and a nonionic surfactant, wherein the concentration of the cellulosic polymer in the aqueous suspension agent is from about 0.0005 w/v % to about 0.003 w/v %, wherein the cellulosic polymer is methylcellulose, wherein the concentration of the nonionic surfactant in the aqueous suspension is from about 0.01 w/v % to about 0.03 w/v %, wherein the nonionic surfactant is tyloxapol, the aqueous suspension agent further comprising zinc chloride and a borate buffer, wherein the concentration of the zinc chloride in the aqueous suspension is from about 0.001% w/v to about 0.005% w/v, wherein the aqueous suspension has a pH of about 6.0 to about 8.0, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.3% w/v to about 1.0% w/v, wherein the (E)-2-(7-trifluoromethylchroman-4-ylidene)-N-(7-hydroxy-5,6,7,8-tetrahydronaphthalen-1-yl)acetamide is (E)-2-(7-trifluoromethylchroman-4-ylidene)-N-((7R)-7-hydroxy-5,6,7,8-tetrahydronaphthalen-1-yl)acetamide, and wherein the aqueous suspension agent is contained in a plastic container.

(Item A1)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; and a nonionic surfactant.

(Item B1)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a nonionic surfactant; and a zinc salt or a silver salt.

(Item B2)

The aqueous suspension agent of any one of the preceding items, wherein the concentration of the nonionic surfactant in the aqueous suspension is from about 0.0001 w/v % to about 0.5 w/v %.

(Item B2a)

The aqueous suspension agent of any one of the preceding items, wherein the concentration of the nonionic surfactant in the aqueous suspension is from about 0.0001 w/v % to about 0.1 w/v %.

(Item B3)

The aqueous suspension agent of any one of the preceding items, wherein the concentration of the nonionic surfactant in the aqueous suspension is from about 0.01 w/v % to about 0.05 w/v %.

(Item B4)

The aqueous suspension agent of any one of the preceding items, wherein the nonionic surfactant is at least one selected from the group consisting of tyloxapol, polysorbate 80, polyethylene glycol monostearate, and polyoxyethylene hydrogenated castor oil.

(Item B5)

The aqueous suspension agent of any one of the preceding items, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof in the aqueous suspension is from about 0.01% w/v to about 5% w/v.

(Item B6)

The aqueous suspension agent of any one of the preceding items, wherein the concentration of the zinc salt or silver salt in the aqueous suspension is from about 0.0001 w/v % to about 0.05 w/v %.

(Item B7)

The aqueous suspension agent of any one of the preceding items, wherein the zinc salt is zinc chloride or zinc sulfate.

(Item B7a)

The aqueous suspension agent of any one of the preceding items, wherein the silver salt is silver nitrate.

(Item B8)

The aqueous suspension agent of any one of the preceding items, further comprising a cellulosic polymer.

(Item B9)

The aqueous suspension agent of the preceding item, wherein the concentration of the cellulosic polymer in the aqueous suspension agent is from about 0.00007 w/v % to about 0.01 w/v %.

(Item B9a)

The aqueous suspension agent of the preceding item, wherein the concentration of the cellulosic polymer in the aqueous suspension agent is from about 0.00007 w/v % to about 0.007 w/v %.

(Item B10)

The aqueous suspension agent of any one of the preceding items, wherein the concentration of the cellulosic polymer in the aqueous suspension agent is from about 0.0001 w/v % to about 0.008 w/v %.

(Item B10a)

The aqueous suspension agent of any one of the preceding items, wherein the concentration of the cellulosic polymer in the aqueous suspension agent is from about 0.0001 w/v % to about 0.005 w/v %.

(Item B11)

The aqueous suspension agent of any one of the preceding items, wherein the cellulosic polymer is at least one selected from the group consisting of methylcellulose, hydroxypropylmethylcellulose, and carboxymethylcellulose.

(Item B12)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide is (E)-2-(7-trifluoromethylchroman-4-ylidene)-N-((7R)-7-hydroxy-5,6,7,8-tetrahydronaphthalen-1-yl) acetamide.

(Item B13)

The aqueous suspension agent of any one of the preceding items, further comprising a borate buffer.

(Item B14)

The aqueous suspension agent of any one of the preceding items, wherein the aqueous suspension has a pH of about 4 to about 8.

(Item B15)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved redispersibility.

(Item B16)

The aqueous suspension agent of any one of the preceding items, wherein the improvement in redispersibility is the redispersion of suspended particles at about 15 or fewer shakes, when evaluated by a shaking operation.

(Item B17)

The aqueous suspension agent of any one of the preceding items, wherein the improvement in redispersibility is the redispersion of suspended particles at about 40 or fewer inversions when evaluated by an inversion operation.

(Item B18)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved stability.

(Item B19)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved redispersibility, and wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has improved stability.

(Item B20)

The aqueous suspension agent of any one of the preceding items, wherein the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof, in the aqueous suspension, has an average particle size of about 1 μm to about 5 μm.

(Item B21)

The aqueous suspension agent of any one of the preceding items, wherein the aqueous suspension agent is contained in a plastic container.

(Item B22)

The aqueous suspension agent of any one of the preceding items, wherein the material of the plastic container is polyethylene or polypropylene.

(Item B23)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a nonionic surfactant; and a zinc salt or a silver salt, wherein the concentration of the nonionic surfactant in the aqueous suspension is from about 0.0001 w/v % to about 0.5 w/v %, wherein the nonionic surfactant is at least one selected from the group consisting of tyloxapol, polysorbate 80, and polyethylene glycol monostearate, wherein the concentration of the zinc salt or silver salt in the aqueous suspension is from about 0.0005% w/v to about 0.01% w/v, wherein the zinc salt or silver salt is at least one selected from the group consisting of zinc chloride, zinc sulfate and silver nitrate, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item B24)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a nonionic surfactant; and a zinc salt or a silver salt, wherein the concentration of the nonionic surfactant in the aqueous suspension is from about 0.01 w/v % to about 0.05 w/v %, wherein the nonionic surfactant is at least one selected from the group consisting of tyloxapol, polysorbate 80, and polyethylene glycol monostearate, wherein the concentration of the zinc salt or silver salt in the aqueous suspension is from about 0.0005% w/v to about 0.01% w/v, wherein the zinc salt or silver salt is at least one selected from the group consisting of zinc chloride, zinc sulfate and silver nitrate, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item B25)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; a nonionic surfactant; and a zinc salt, wherein the concentration of the nonionic surfactant in the aqueous suspension is from about 0.01 w/v % to about 0.03 w/v %, wherein the nonionic surfactant is tyloxapol, wherein the concentration of the zinc salt in the aqueous suspension is from about 0.001 w/v % to about 0.005 w/v %, wherein the zinc salt is zinc chloride, the aqueous suspension agent further comprising a borate buffer, wherein the aqueous suspension has a pH of about 6.0 to about 8.0, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.3% w/v to about 1.0% w/v,
wherein the (E)-2-(7-trifluoromethylchroman-4-ylidene)-N-(7-hydroxy-5,6,7,8-tetrahydronaphthalen-1-yl)acetamide is (E)-2-(7-trifluoromethylchroman-4-ylidene)-N-((7R)-7-hydroxy-5,6,7,8-tetrahydronaphthalen-1-yl) acetamide, and
wherein the aqueous suspension agent is contained in a plastic container.

(Item C1)

An aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof; and tyloxapol.

(Item D1a)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:
mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, and a nonionic surfactant to prepare an aqueous suspension agent.

(Item D1b)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:
adding a cellulosic polymer and a nonionic surfactant to an aqueous suspension agent comprising (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof.

(Item D2)

The method of the preceding item, wherein the concentration of the cellulosic polymer in the aqueous suspension agent is from about 0.00007 w/v % to about 0.01 w/v %.

(Item D2a)

The method of the preceding item, wherein the concentration of the cellulosic polymer in the aqueous suspension agent is from about 0.00007 w/v % to about 0.007 w/v %.

(Item D3)

The method of any one of the preceding items, wherein the concentration of the cellulosic polymer in the aqueous suspension agent is from about 0.0001 w/v % to about 0.008 w/v %.

(Item D3a)

The method of any one of the preceding items, wherein the concentration of the cellulosic polymer in the aqueous suspension agent is from about 0.0001 w/v % to about 0.005 w/v %.

(Item D4)

The method of any one of the preceding items, wherein the cellulosic polymer is at least one selected from the group consisting of methylcellulose, hydroxypropylmethylcellulose, and carboxymethylcellulose.

(Item D5)

The method of any one of the preceding items, wherein the concentration of the nonionic surfactant in the aqueous suspension is from about 0.0001 w/v % to about 0.5 w/v %.

(Item D6)

The method of any one of the preceding items, wherein the concentration of the nonionic surfactant in the aqueous suspension is from about 0.0001 w/v % to about 0.1 w/v %.

(Item D6a)

The method of any one of the preceding items, wherein the concentration of the nonionic surfactant in the aqueous suspension is from about 0.01 w/v % to about 0.05 w/v %.

(Item D7)

The method of any one of the preceding items, wherein the nonionic surfactant is at least one selected from the group consisting of tyloxapol, polysorbate 80, polyethylene glycol monostearate, and polyoxyethylene hydrogenated castor oil.

(Item D8)

The method of any one of the preceding items, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof in the aqueous suspension is from about 0.01% w/v to about 5% w/v.

(Item D9)

The method of any one of the preceding items, further comprising the step of mixing a zinc salt or a silver salt.

(Item D10)

The method of any one of the preceding items, wherein the concentration of the zinc salt or silver salt in the aqueous suspension is from about 0.0001 w/v % to about 0.05 w/v %.

(Item D11)

The method of any one of the preceding items, wherein the zinc salt is zinc chloride or zinc sulfate.

(Item D11a)

The method of any one of the preceding items, wherein the silver salt is silver nitrate.

(Item D12)

The method of any one of the preceding items, wherein the (E)-2-(7-trifluoromethylchroman-4-ylidene)-N-(7-hydroxy-5,6,7,8-tetrahydronaphthalen-1-yl)acetamide is (E)-2-(7-trifluoromethylchroman-4-ylidene)-N-((7R)-7-hydroxy-5,6,7,8-tetrahydronaphthalen-1-yl)acetamide.

(Item D13)

The method of any one of the preceding items, further comprising the step of mixing a borate buffer.

(Item D14)

The method of any one of the preceding items, wherein the aqueous suspension has a pH of about 4 to about 8.

(Item D15)

The method of any one of the preceding items, wherein the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, has improved redispersibility.

(Item D16)

The method of any one of the preceding items, wherein the improvement in redispersibility comprises the redispersion of suspended particles at about 15 or fewer shakes, when evaluated by a shaking operation.

(Item D17)

The method of any one of the preceding items, wherein the improvement in redispersibility comprises the redispersion of suspended particles at about 40 or fewer inversions when evaluated by an inversion operation.

(Item D18)

The method of any one of the preceding items, wherein the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, has improved stability.

(Item D19)

The method of any one of the preceding items, wherein the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, has improved redispersibility, and wherein the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, has improved stability.

(Item D20)

The method of any one of the preceding items, wherein the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, has an average particle size of about 1 μm to about 5 μm.

(Item D21)

The method of any one of the preceding items, wherein the aqueous suspension agent is contained in a plastic container.

(Item D22)

The method of any one of the preceding items, wherein the material of the plastic container is polyethylene or polypropylene.

(Item D23)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, and a nonionic surfactant to prepare an aqueous suspension agent, wherein the concentration of the cellulosic polymer in the aqueous suspension agent is from about 0.0001 w/v % to about 0.005 w/v %, wherein the cellulosic polymer is at least one selected from the group consisting of methylcellulose, hydroxypropylmethylcellulose, and carboxymethylcellulose, wherein the concentration of the nonionic surfactant in the aqueous suspension is from about 0.01 w/v % to about 0.05 w/v %, wherein the nonionic surfactant is at least one selected from the group consisting of tyloxapol, polysorbate 80, and polyethylene glycol monostearate, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item D24)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, and a nonionic surfactant to prepare an aqueous suspension agent, the method further comprising the step of: blending a zinc salt or silver salt and a borate buffer, wherein the concentration of the cellulosic polymer in the aqueous suspension agent is from about 0.0001 w/v % to about 0.005 w/v %, wherein the cellulosic polymer is at least one selected from the group consisting of methylcellulose, hydroxypropylmethylcellulose, and carboxymethylcellulose, wherein the concentration of the nonionic surfactant in the aqueous suspension is from about 0.01 w/v % to about 0.05 w/v %, wherein the nonionic surfactant is at least one selected from the group consisting of tyloxapol, polysorbate 80, and polyethylene glycol monostearate, wherein the zinc salt or silver salt is at least one selected from the group consisting of zinc chloride, zinc sulfate and silver nitrate, wherein the concentration of the zinc salt or silver salt in the aqueous suspension is from about 0.0005% w/v to about 0.01% w/v, wherein the aqueous suspension has a pH of about 4 to about 8, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item D25)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, and a nonionic surfactant to prepare an aqueous suspension agent, the method further comprising the step of mixing zinc chloride and a borate buffer, wherein the concentration of the cellulosic polymer in the aqueous suspension agent is from about 0.0001 w/v % to about 0.005 w/v %, wherein the cellulosic polymer is methylcellulose, wherein the concentration of the nonionic surfactant in the aqueous suspension is from about 0.01 w/v % to about 0.05 w/v %, wherein the nonionic surfactant is tyloxapol, wherein the concentration of the zinc chloride in the aqueous suspension is from about 0.0005 w/v % to about 0.01 w/v %, wherein the aqueous suspension has a pH of about 4 to about 8, and wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.01% w/v to about 5% w/v.

(Item D26)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, and a nonionic surfactant to prepare an aqueous suspension agent, the method further comprising the step of mixing a borate buffer, wherein the concentration of the cellulosic polymer in the aqueous suspension agent is from about 0.0005 w/v % to about 0.003 w/v %, wherein the cellulosic polymer is methylcellulose, wherein the concentration of the nonionic surfactant in the aqueous suspension is from about 0.01 w/v % to about 0.03 w/v %, wherein the nonionic surfactant is tyloxapol, wherein the aqueous suspension has a pH of about 6.0 to about 8.0, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.3% w/v to about 1.0% w/v, and wherein the (E)-2-(7-trifluoromethylchroman-4-ylidene)-N-(7-hydroxy-5,6,7,8-tetrahydronaphthalen-1-yl)acetamide is (E)-2-(7-trifluoromethylchroman-4-ylidene)-N-((7R)-7-hydroxy-5,6,7,8-tetrahydronaphthalen-1-yl) acetamide.

(Item D27)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, and a nonionic surfactant to prepare an aqueous suspension agent, the method further comprising the step of mixing zinc chloride and a borate buffer, wherein the concentration of the cellulosic polymer in the aqueous suspension agent is from about 0.0005 w/v % to about 0.003 w/v %, wherein the cellulosic polymer is methylcellulose, wherein the concentration of the nonionic surfactant in the aqueous suspension is from about 0.01 w/v % to about 0.03 w/v %, wherein the nonionic surfactant is tyloxapol, wherein the concentration of the zinc chloride in the aqueous suspension is from about 0.001% w/v to about 0.005% w/v, wherein the aqueous suspension has a pH of about 6.0 to about 8.0, wherein the concentration of the (E)-2-(7-trifluoromethylchroman-4-ylidene)-N-(7-hydroxy-5,6,7,8-tetrahydronaphthalen-1-yl)acetamide or the pharmaceutically acceptable salt or solvate thereof, in the aqueous suspension, is from about 0.3% w/v to about 1.0% w/v, wherein the (E)-2-(7-trifluoromethylchroman-4-ylidene)-N-(7-hydroxy-5,6,7,8-tetrahydronaphthalen-1-yl)acetamide is (E)-2-(7-trifluoromethylchroman-4-ylidene)-N-((7R)-7-hydroxy-5,6,7,8-tetrahydronaphthalen-1-yl) acetamide, and wherein the aqueous suspension agent is contained in a plastic container.

(Item E1)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, and a nonionic surfactant to prepare an aqueous suspension agent.

(Item F1)

A method of improving the redispersibility of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a nonionic surfactant, and a zinc salt or silver salt to prepare an aqueous suspension agent.

(Item G1)

A method of improving the stability of an aqueous suspension agent comprising: (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, the method comprising the step of:

mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, and tyloxapol to prepare an aqueous suspension agent.

Advantageous Effects of Invention

The present disclosure can provide an aqueous suspension agent having excellent redispersibility.

The present disclosure provides the above feature to be able to suppress the phenomenon that suspended particles are not uniformly dispersed, and stably administer a required amount of an active ingredient, thereby achieving stable and sufficient exertion of pharmacological effects. It contributes to improving patient adherence and convenience.

BRIEF DESCRIPTION OF DRAWINGS

FIG. 1 is a graph showing the transmittance of each bottle (colorless PE, colorless PP, brown PE) at each wavelength.

DESCRIPTION OF EMBODIMENTS

The present disclosure will be described hereinafter. Throughout the entire specification, a singular expression should be understood as encompassing the concept thereof in the plural form, unless specifically noted otherwise. Thus, singular articles (e.g., "a", "an", "the", and the like in case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definitions

As used herein, "about" means±10% of the numerical value that follows, unless otherwise specified.

As used herein, "or" is used when "at least one or more" of the matters listed in the sentence can be employed. When explicitly described herein as "within the range of two values", the range also includes the two values themselves.

As used herein, the term "aqueous suspension" is used in the same sense as the term used in the subject field, and is a liquid-state agent at least partially comprising water, where the agent refers to an agent in which the components to be mixed are in a suspended state, and in which solid particles are in a state of being present in a liquid. (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, has very low solubility in water. Therefore, in the aqueous suspension agent of the present disclosure, (E)-2-(7-trifluoromethylchroman-4-ylidene)-N-(7-hydroxy-5,6,7,8-tetrahydronaphthalen-1-yl) acetamide, or the pharmaceutically acceptable salt or solvate thereof, becomes suspended particles, but remains partially dissolved.

As used herein, the term "pharmaceutically acceptable salt" refers to the relatively non-toxic, inorganic or organic acid addition salts or inorganic or organic base addition salts of the compounds of the present disclosure.

As used herein, the term "solvate" refers to a compound of the present disclosure or a pharmaceutically acceptable salt thereof and any solvent that forms a single group by interaction, and encompasses, for example, solvates with organic solvents (e.g., alcohol (ethanol, etc.) solvates), hydrates, and the like. When forming a hydrate, it may be coordinated with any number of water molecules. Examples of hydrates include monohydrates and dihydrates.

As used herein, the term "redispersibility" refers to the ease with which particles, generated by sedimentation in the solvent of a liquid containing particles, such as a suspension, stored for a certain period of time (in the case of a suspension, they are also called "suspended particles"), are uniformly redispersed throughout the liquid. As used herein, the "redispersibility" is evaluated by a test using a shaking operation or an inversion operation.

As used herein, the term "shaking operation" refers to an operation of holding a container filled with "aqueous suspension agent" and shaking it vertically. In the "shaking operation", the container is shaken vertically 10 to 15 cm wide, where one shaking operation is defined as the period from when the container is shaken up until it returns to its original position, and the container is shaken five times at a speed of 1.1 seconds/set as one set. The redispersibility test by "shaking operation" is performed with 3 to 5 samples per formulation, where the average number of sets is calculated from the number of sets required for redispersion of each sample, and the number of times converted to the number of shakings is used.

As used herein, the term "inversion operation" refers to an operation of holding a container filled with an "aqueous suspension agent" and turning it upside down. The redispersibility test by the "inversion operation" is performed with 3 to 5 samples per formulation. The operation of turning the container upside down by 180 degrees at a speed of 1 second/time and then turning it over again by 180 degrees to make it upright is defined as one inversion.

As used herein, the term "improved redispersibility" means that particles that have sedimented in a liquid containing particles such as suspensions are easily dispersed again. In the comparison of any formulations, it can be said that the redispersibility has been improved when the number of times of the "shaking operation" or "inversion operation" is decreased.

As used herein, the term "stability" refers to the degree to which the content of (E)-2-(7-trifluoromethylchroman-4- ylidene)-N-(7-hydroxy-5,6,7,8-tetrahydronaphthalen-1-yl) acetamide, or a pharmaceutically acceptable salt or solvate thereof, dissolved and/or suspended in an aqueous suspension is maintained without being altered by decomposition or the like after storage for a certain period of time. In addition, as used herein, the "stability" is evaluated by the content maintenance ratio, which is the ratio of the content of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, in the aqueous suspension agent stored for a certain period after preparation to the content of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, in the aqueous suspension agent immediately after preparation. Typically, this evaluation is determined by evaluating the content retention rate of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, dissolved in the aqueous suspension agent.

As used herein, the term "improved stability" means that, in comparison to any formulations, when the content retention rate is high, the stability is improved.

As used herein, the term "average particle size of suspended particles" refers to the median size ($D_{50}$) of the particles of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, and is a value measured using a laser diffraction particle size distribution analyzer.

As used herein, the term "cellulosic polymer" is one type of water-soluble polymer, and refers to a cellulose derivative in which hydroxyl groups of cellulose are partially converted to other substituents. For example, cellulosic polymers include methyl cellulose (hereinafter sometimes referred to as "MC"), hydroxypropylmethyl cellulose, carboxymethyl cellulose (hereinafter sometimes referred to as "CMC"), ethyl cellulose, propyl cellulose, hydroxymethyl cellulose, hydroxyethyl cellulose, hydroxypropyl cellulose, sulfonated cellulose derivatives and the like.

As used herein, the term "nonionic surfactant" is also called a nonionic surfactant, and refers to a surfactant in which the portion of the hydrophilic group is nonionic. Whether a surfactant is a nonionic surfactant can be easily determined by those skilled in the art, and can be determined by confirming that it does not ionize (does not exhibit ionicity) when dissolved in water. For example, nonionic surfactants include tyloxapol, polyoxyl stearates (polyethylene glycol monostearate, polyethylene glycol monostearate 40 (MYS-40), polyethylene glycol monostearate 400, etc.), polyoxyethylene sorbitan fatty acid esters (polyoxyethylene sorbitan monooleate (polysorbate 80), polyoxyethylene sorbitan monolaurate, polyoxyethylene sorbitan monopalmitate, polyoxyethylene sorbitan monostearate, polyoxyethylene sorbitan tristearate rate, etc.), and polyoxyethylene hydrogenated castor oils (polyoxyethylene hydrogenated castor oil 10, polyoxyethylene hydrogenated castor oil 40, polyoxyethylene hydrogenated castor oil 50, polyoxyethylene hydrogenated castor oil 60 (HCO-60), and the like).

As used herein, the term "zinc salt" refers to a salt (a compound of zinc and an organic acid or an inorganic acid) containing a zinc ion ($Zn^{2+}$) as a constituent ion, or an oxide of zinc. For example, zinc salts include zinc halides such as zinc chloride, zinc bromide or zinc fluoride, zinc sulfate, zinc acetate, zinc phosphate, zinc carbonate, zinc hydroxide, zinc citrate, zinc lactate, zinc gluconate, zinc oxide, or hydrates thereof.

As used herein, the term "silver salt" refers to a salt (a compound of silver and an organic acid or an inorganic acid) containing silver ions (Ag+) as constituent ions, or an oxide of silver. For example, silver salts include silver nitrate, silver bromide, silver oxide, silver acetate, silver carbonate, silver citrate, silver lactate, silver phosphate, silver oxalate, silver thiosulfate, silver protein, or hydrates thereof.
(Aqueous Suspension Agent)

In the present disclosure, an aqueous suspension agent can be provided, which comprises (E)-2-(7-trifluoromethyl-chroman-4-ylidene)-N-(7-hydroxy-5,6,7,8-tetrahydronaph-thalen-1-yl)acetamide, or a pharmaceutically acceptable salt or solvate thereof, and a nonionic surfactant.

In the present disclosure, an aqueous suspension agent can be provided, which comprises (E)-2-(7-trifluoromethyl-chroman-4-ylidene)-N-(7-hydroxy-5,6,7,8-tetrahydronaph-thalen-1-yl)acetamide, or a pharmaceutically acceptable salt or solvate thereof, a cellulosic polymer, and a nonionic surfactant.

In the present disclosure, an aqueous suspension agent can be provided, which comprises (E)-2-(7-trifluoromethyl-chroman-4-ylidene)-N-(7-hydroxy-5,6,7,8-tetrahydronaph-thalen-1-yl)acetamide, or a pharmaceutically acceptable salt or solvate thereof, a nonionic surfactant, and a zinc salt or a silver salt.

In the present disclosure, an aqueous suspension agent can be provided, which comprises (E)-2-(7-trifluoromethyl-chroman-4-ylidene)-N-(7-hydroxy-5,6,7,8-tetrahydronaph-thalen-1-yl)acetamide, or a pharmaceutically acceptable salt or solvate thereof, a cellulosic polymer, a nonionic surfac-tant, and a zinc salt or a silver salt.

In one aspect of the disclosure, a method of improving the redispersibility of suspended particles of (E)-2-(7-trifluo-romethylchroman-4-ylidene)-N-(7-hydroxy-5,6,7,8-tetrahy-dronaphthalen-1-yl)acetamide, or a pharmaceutically acceptable salt or solvate thereof, can be provided, the method comprising the step of mixing (E)-2-(7-trifluorom-ethylchroman-4-ylidene)-N-(7-hydroxy-5,6,7,8-tetrahy-dronaphthalen-1-yl)acetamide or a pharmaceutically accept-able salt or solvate thereof, and a nonionic surfactant to prepare an aqueous suspension agent.

In other aspects, a method of improving the redispersibil-ity of suspended particles of (E)-2-(7-trifluoromethylchro-man-4-ylidene)-N-(7-hydroxy-5,6,7,8-tetrahydronaphtha-len-1-yl)acetamide, or a pharmaceutically acceptable salt or solvate thereof, can be provided, the method comprising the step of mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, and a nonionic surfactant to prepare an aqueous suspension agent.

In other aspects, a method of improving the redispersibil-ity of suspended particles of (E)-2-(7-trifluoromethylchro-man-4-ylidene)-N-(7-hydroxy-5,6,7,8-tetrahydronaphtha-len-1-yl)acetamide, or a pharmaceutically acceptable salt or solvate thereof, can be provided, the method comprising the step of mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a nonionic surfactant, and a zinc salt or a silver salt to prepare an aqueous suspension agent.

In other aspects, a method of improving the redispersibil-ity of suspended particles of (E)-2-(7-trifluoromethylchro-man-4-ylidene)-N-(7-hydroxy-5,6,7,8-tetrahydronaphthalen-1-yl)acetamide, or a pharmaceutically acceptable salt or solvate thereof, can be provided, the method comprising the step of mixing (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, a cellulosic polymer, a nonionic surfactant, and a zinc salt or a silver salt to prepare an aqueous suspension agent.

In another aspect of the present disclosure, a method of improving the redispersibility of an aqueous suspension agent comprising (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, the method comprising the step of adding a cellulosic polymer to an aqueous suspension agent comprising (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof.

In another aspect of the present disclosure, a method of improving the redispersibility of an aqueous suspension agent comprising (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, the method comprising the step of adding a nonionic surfactant to an aqueous suspension agent comprising (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof.

In another aspect of the present disclosure, a method of improving the redispersibility of an aqueous suspension agent comprising (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, the method comprising the step of adding a zinc salt or a silver salt to an aqueous suspension agent comprising (E)-2-(7-trifluoromethylchroman-4-ylidene)-N-(7-hydroxy-5,6,7,8-tetrahydronaphthalen-1-yl) acetamide or a pharmaceutically acceptable salt or solvate thereof.

In another aspect of the present disclosure, a method of improving the redispersibility of an aqueous suspension agent comprising (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, the method comprising the step of adding a cellulosic polymer and a nonionic surfactant to an aqueous suspension agent comprising (E)-2-(7-trifluorom-ethylchroman-4-ylidene)-N-(7-hydroxy-5,6,7,8-tetrahy-dronaphthalen-1-yl)acetamide or a pharmaceutically accept-able salt or solvate thereof.

In another aspect of the present disclosure, a method of improving the redispersibility of an aqueous suspension agent comprising (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, the method comprising the step of adding a nonionic surfactant and a zinc salt or a silver salt to an aqueous suspension agent comprising (E)-2-(7-trifluo-romethylchroman-4-ylidene)-N-(7-hydroxy-5,6,7,8-tetrahy-dronaphthalen-1-yl)acetamide or a pharmaceutically accept-able salt or solvate thereof.

In another aspect of the present disclosure, a method of improving the redispersibility of an aqueous suspension agent comprising (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, the method comprising the step of adding a cellulosic polymer and a zinc salt or a silver salt to an aqueous suspension agent comprising (E)-2-(7-trifluo-romethylchroman-4-ylidene)-N-(7-hydroxy-5,6,7,8-tetrahy-dronaphthalen-1-yl)acetamide or a pharmaceutically accept-able salt or solvate thereof.

In another aspect of the present disclosure, a method of improving the redispersibility of an aqueous suspension agent comprising (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, the method comprising the step of adding a cellulosic polymer, a nonionic surfactant, and a zinc salt or a silver salt to an aqueous suspension agent comprising (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof.

(E)-2-(7-trifluoromethylchroman-4-ylidene)-N-(7-hy-droxy-5,6,7,8-tetrahydronaphthalen-1-yl)acetamide includes R body (CAS. No. 920332-28-1), S body (CAS. No. 920332-29-2), or racemic body (CAS. No. 920332-27-0), and more preferably, R body ((E)-2-(7-trifluoromethyl-chroman-4-ylidene)-N-((7R)-7-hydroxy-5,6,7,8-tetrahy-dronaphthalen-1-yl)acetamide (which is also referred to as Compound (1) in the present disclosure)).

The pharmaceutically acceptable salt of the compound of the present disclosure is not particularly limited as long as it is a salt that is pharmaceutically acceptable. Specifically, examples of the pharmaceutically acceptable salts include: mineral acids such as hydrochloric acid, hydrobromic acid, hydroiodic acid, sulfuric acid, nitric acid and phosphoric acid; organic carboxylic acids such as formic acid, acetic acid, propionic acid, butyric acid, valeric acid, enanthic acid, capric acid, myristic acid, palmitic acid, stearic acid, lactic acid, sorbic acid, mandelic acid and other aliphatic mono-carboxylic acids, benzoic acid, salicylic acid and other aromatic monocarboxylic acids, oxalic acid, malonic acid, succinic acid, fumaric acid, maleic acid, malic acid, tartaric acid and other aliphatic dicarboxylic acids, citric acid and other aliphatic tricarboxylic acids; acid addition salts with methanesulfonic acid, ethanesulfonic acid, 2-hydroxy-ethanesulfonic acid and other aliphatic sulfonic acids, with organic sulfonic acids including benzenesulfonic acid, p-toluenesulfonic acid and other aromatic sulfonic acids, and the like; inorganic base addition salts with metals including alkali metals such as sodium, potassium, magne-sium and calcium, or alkaline earth metals; organic base addition salts such as methylamine, ethylamine, etha-nolamine, pyridine, lysine, arginine and ornithine, and the like.

These salts can be obtained by a conventional method, for example, by mixing an equivalent amount of the compound of the present disclosure with a solution containing the desired acid or base and collecting the desired salt by filtration or distilling off the solvent. Furthermore, the com-pounds of the disclosure or salts thereof can form solvates with water or solvents such as ethanol.

(E)-2-(7-trifluoromethylchroman-4-ylidene)-N-(7-hy-droxy-5,6,7,8-tetrahydronaphthalen-1-yl)acetamide has an excellent Transient Receptor Potential Vanilloid 1 (herein-after referred to as "TRPV1". TRPV1 is also referred to as "transient receptor potential vanilloid 1" or "vanilloid recep-tor 1 (VR1)") antagonistic action.

The R body (Compound (1)), S body or racemic body of (E)-2-(7-trifluoromethylchroman-4-ylidene)-N-(7-hydroxy-5,6,7,8-tetrahydronaphthalen-1-yl)acetamide is described in International Publication No. WO 2007/010383 Pamphlet, Japanese Patent No. 4754566, Japanese Patent No. 6230743, International Publication No. WO 2018/221543 Pamphlet, Japanese Patent No. 6830569, International Publication No. WO 2021/038889 Pamphlet, and International Publication No. WO 2021/039023 Pamphlet. The R body (Compound (1)), S body or racemic body can be manufactured by a manufacturing method described in these publications. The contents of the publication are incorporated herein in their entirety.

TRPV1 is a TRP channel that has been cloned as a cation channel that responds to capsaicin from the dorsal root ganglion (DRG), has sensitivity to heat of 43° C. or higher and protons, and is being studied as a key molecule of nociception (Seikagaku. The journal of Japanese Biochemi-cal Society, Vol. 85, No. 7: 561-565). TRPV1 is known to increase its activity during inflammation or tissue damage and induce hyperalgesia. Therefore, TRPV1 is of interest as a potential drug target for pain therapy.

It has been reported that TRPV1 antagonists are effective against various pain models such as inflammatory pain, neuropathic pain and osteoarthritis (Biochemistry, Vol. 85, Vol. 7: 561-565).

In the present disclosure, (E)-2-(7-trifluoromethylchro-man-4-ylidene)-N-(7-hydroxy-5,6,7,8-tetrahydronaphtha-len-1-yl)acetamide, or a pharmaceutically acceptable salt or solvate thereof, is mixed with a cellulosic polymer and a nonionic surfactant to form an aqueous suspension agent so that the redispersibility of the (E)-2-(7-trifluoromethylchro-man-4-ylidene)-N-(7-hydroxy-5,6,7,8-tetrahydronaphtha-len-1-yl)acetamide, or a pharmaceutically acceptable salt or solvate thereof, can have improved redispersibility.

In other aspects of the present disclosure, a composition for improving the redispersibility of an aqueous suspension agent of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, can be provided, where the composition comprises a nonionic surfactant.

In other aspects of the present disclosure, a composition for improving the redispersibility of an aqueous suspension agent of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, can be provided, where the composition comprises a cellulosic polymer.

In other aspects of the present disclosure, a composition for improving the redispersibility of an aqueous suspension agent of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, can be provided, where the composition comprises a cellulosic polymer and a nonionic surfactant.

In other aspects of the present disclosure, a composition for improving the redispersibility of an aqueous suspension agent of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, can be provided, where the composition comprises a cellulosic polymer and a zinc salt or a silver salt.

Further, in other aspects of the present disclosure, a composition for improving the redispersibility of an aqueous suspension agent of (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, can be provided, where the composition comprises a nonionic surfactant and a zinc salt or a silver salt.

In other aspects of the present disclosure, a composition for improving the redispersibility of an aqueous suspension agent of (E)-2-(7-trifluoromethylchroman-4-ylidene)-N-(7- hydroxy-5,6,7,8-tetrahydronaphthalen-1-yl)acetamide, or a pharmaceutically acceptable salt or solvate thereof, can be provided, where the composition comprises a cellulosic polymer, a nonionic surfactant and a zinc salt or a silver salt.

In one embodiment of the present disclosure, (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, can be present in the aqueous suspension of the present disclosure at concentrations typically from about 0.01 w/v % to about 5 w/v %, preferably from about 0.1 w/v % to about 3 w/v %, more preferably from about 0.2 w/v % to about 2 w/v %, particularly preferably from about 0.2 w/v % to about 1.5 w/v %, and still more preferably from about 0.3 w/v % to about 1.0 w/v %.

In one embodiment of the present disclosure, when the R body of (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, is used, it can be present in the aqueous suspension agent of the present disclosure at concentrations typically from about 0.01 w/v % to about 5 w/v %, preferably from about 0.1 w/v % to about 3 w/v %, more preferably from about 0.2 w/v % to about 2 w/v %, particularly preferably from about 0.2 w/v % to about 1.5 w/v %, and still more preferably from about 0.3 w/v % to about 1.0 w/v %.

In one embodiment of the present disclosure, the cellulosic polymer is not particularly limited as long as it is pharmaceutically acceptable, and the cellulosic polymer can include methylcellulose, hydroxypropylmethylcellulose, carboxymethylcellulose, ethylcellulose, propylcellulose, hydroxymethylcellulose, hydroxyethylcellulose, hydroxypropylcellulose, sulfonated cellulose derivatives, or pharmaceutically acceptable salts thereof, and the like. In addition, these cellulosic polymer compounds may be used singly or in combination of two or more. The cellulosic polymer is preferably methylcellulose, hydroxypropylmethylcellulose, or carboxymethylcellulose from the viewpoint of redispersibility of the aqueous suspension agent.

The cellulosic polymer is a linear water-soluble polymer having glucose as a basic unit. When a cellulosic polymer is added to an aqueous suspension containing Compound (1), the cellulosic polymer is appropriately distributed around the suspended particles in the presence of the nonionic surfactant. In addition, cellulosic polymers are known to form a sheet structure between celluloses, and without being bound by theory, it is thought that this sheet structure covering the suspended particles maintains an appropriate distance between the particles and contributes to the formation of a bulky sedimentation layer. In addition, without being bound by theory, when the suspended particles settle, it is thought that setting the cellulosic polymer to any concentration relative to the suspended particles allows the cellulosic polymer to act as an appropriate steric hindrance, thereby forming a bulky sedimentation layer and preparing an aqueous suspension agent with favorable redispersibility. Therefore, in one embodiment of present disclosure, the use of a cellulosic polymer can be expected to prepare an aqueous suspension agent having excellent redispersibility.

On the other hand, carboxyvinyl polymer and polyvinylpyrrolidone have main chain structures of acrylic acid and N-vinyl-2-pyrrolidone, respectively, and they are water-soluble polymers that do not have a three-dimensional structure such as a sheet structure. When these water-soluble polymers are distributed around suspended particles, the effect of maintaining the distance between suspended particles is considered to be weaker than that of cellulosic polymers.

In one embodiment of the present disclosure, the methyl cellulose used is not particularly limited, but any methyl cellulose having different substitution rates, molecular weights, viscosities, etc., of the methoxy group may be used. These can be used singly or in combination of two or more. The degree of substitution of methoxy groups in methylcellulose is usually in the range of about 20 to about 40%, preferably in the range of 26 to 33%. In addition, the viscosity of methylcellulose (refers to viscosity of 2 wt % aqueous solution at 20° C.) is typically from 1 to 10,000 mPa-s, preferably from 3 to 3,000 mPa-s, more preferably from 4 to 1,500 mPa-s, particularly preferably from 3 to 50 mPa-s, and further preferably from 10 to 20 mPa-s. Examples of commercially available products include Metolose SM-4, Metolose SM-15, Metolose SM-25, SM-100, SM-400, Metolose SM-1500, SM-4000 (Shin-Etsu Chemical Co., Ltd.) and the like.

In one embodiment of the present disclosure, the cellulosic polymer can be present in the aqueous suspension agent of the present disclosure typically at a concentration of from about 0.00007% w/v to about 0.01% w/v, preferably from about 0.0001 w/v % to about 0.008 w/v %, more preferably from about 0.0005 w/v % to about 0.005 w/v %, particularly preferably from about 0.0006 w/v % to about 0.003 w/v %, still more preferably from about 0.0007 w/v % to about 0.002 w/v %, and most preferably from about 0.0008 w/v % to about 0.001 w/v %.

In other embodiments of the present disclosure, the cellulosic polymer can be present in the aqueous suspension agent of the present disclosure typically at a concentration of from about 0.00007 w/v % to about 0.007 w/v %, preferably from about 0.0001 w/v % to about 0.005 w/v %, more preferably from about 0.0003 w/v % to about 0.004 w/v %, particularly preferably from about 0.0005 w/v % to about 0.003 w/v %, still more preferably about 0.0007 w/v % to about 0.001 w/v %, and most preferably about 0.001 w/v %.

In one embodiment of the present disclosure, when methyl cellulose is used as the cellulosic polymer, it can be present in the aqueous suspension agent of the present disclosure typically at a concentration of from about 0.00007 w/v % to about 0.007 w/v %, preferably from about 0.0001 w/v % to about 0.005 w/v %, more preferably from about 0.0003 w/v % to about 0.004 w/v %, particularly preferably from about 0.0005 w/v % to about 0.003 w/v %, still more preferably from about 0.0007 w/v % to about 0.001 w/v %, and most preferably about 0.001 w/v %.

In one embodiment of the present disclosure, the nonionic surfactant is not particularly limited as long as it is pharmaceutically acceptable, and includes tyloxapol, polyoxyl stearates (polyethylene glycol monostearate, polyethylene glycol monostearate 40 (MYS-40), polyethylene glycol monostearate 400, etc.), polyoxyethylene sorbitan fatty acid esters (polyoxyethylene sorbitan monooleate (polysorbate 80), polyoxyethylene sorbitan monolaurate, polyoxyethylene sorbitan monopalmitate, polyoxyethylene sorbitan monostearate, polyoxyethylene sorbitan tristearate rate, etc.), and polyoxyethylene hydrogenated castor oils (polyoxyethylene hydrogenated castor oil 10, polyoxyethylene hydrogenated castor oil 40, polyoxyethylene hydrogenated castor oil 50, polyoxyethylene hydrogenated castor oil 60 (HCO-60), and the like). In addition, these nonionic surfactants may be used singly or in combination of two or more. The nonionic surfactants are preferably tyloxapol, polysorbate 80, polyethylene glycol monostearate, and polyoxyethylene hydrogenated castor oil 60, more preferably tyloxapol, polysorbate 80 and polyethylene glycol monostearate, and still more preferably tyloxapol, from the viewpoint of the redispersibility or stability of the aqueous suspension agent.

In one embodiment of the present disclosure, the nonionic surfactant can be present in the aqueous suspension agent of the present disclosure at a concentration of from about 0.0001 w/v % to about 0.5 w/v %, preferably from about 0.0001 w/v % to about 0.1 w/v %, and more preferably from about 0.01 w/v % to about 0.005 w/v %.

In other embodiments of the present disclosure, the nonionic surfactant can be present in the aqueous suspension agent of the present disclosure at a concentration of from about 0.0001 w/v % to about 0.5 w/v %, preferably from about 0.005 w/v % to about 0.1 w/v %, more preferably from about 0.01 w/v % to about 0.05 w/v %, and particularly preferably from about 0.01 w/v % to about 0.03 w/v %.

In one embodiment of the present disclosure, when tyloxapol is used as the nonionic surfactant, it can be present in the aqueous suspension agent of the present disclosure at a concentration of from about 0.0001 w/v % to about 0.5 w/v %, preferably from about 0.005 w/v % to about 0.1 w/v %, more preferably from about 0.01 w/v % to about 0.05 w/v %, and particularly preferably from about 0.01 w/v % to about 0.03 w/v %.

In one embodiment of the present disclosure, zinc salts that can be added to the aqueous suspension agent of the present disclosure include zinc halides such as zinc chloride, zinc bromide or zinc fluoride, zinc sulfate, zinc acetate, zinc phosphate, zinc carbonate, zinc hydroxide, zinc citrate, zinc lactate, zinc gluconate, zinc oxide, or hydrates thereof.

In one embodiment of the present disclosure, the zinc salt can be present in the aqueous suspension agent of the present disclosure at a concentration of from about 0.0001 w/v % to about 0.05 w/v %, more preferably from about 0.0005 w/v % to about 0.01 w/v %, and particularly preferably from about 0.001 w/v % to about 0.005 w/v %.

In one embodiment of the present disclosure, when zinc chloride is used as the zinc salt, it can be present in the aqueous suspension agent of the present disclosure at a concentration of from about 0.0001 w/v % to about 0.05 w/v %, more preferably from about 0.0005 w/v % to about 0.01 w/v %, and particularly preferably from about 0.001 w/v % to about 0.005 w/v %.

In one embodiment of the present disclosure, silver salts that can be added to the aqueous suspension agent of the present disclosure include silver nitrate, silver bromide, silver oxide, silver acetate, silver carbonate, silver citrate, silver lactate, silver phosphate, silver oxalate, silver thiosulfate, silver protein, or hydrates thereof.

In one embodiment of the present disclosure, the silver salt can be present in the aqueous suspension agent of the present disclosure at a concentration of from about 0.0001 w/v % to about 0.05 w/v %, more preferably from about 0.0005 w/v % to about 0.01 w/v %, and particularly preferably from about 0.001 w/v % to about 0.005 w/v %.

(Redispersibility)

(E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, has low solubility in water; thus, in the absence of dispersing agents such as nonionic surfactants, ionic surfactants, or water-soluble polymers, the particles float on the surface of the water, making it impossible to prepare an aqueous suspension. In addition, when using a dispersing agent other than a nonionic surfactant, it is necessary to blend the dispersing agent at a concentration substantially exceeding the pharmaceutically acceptable concentration. Therefore, it is essential to blend a nonionic surfactant into the aqueous suspension agent. According to the present disclosure, although a nonionic surfactant is present as a dispersing agent, an aqueous suspension agent having improved redispersibility can be provided by blending any amount of a cellulosic polymer.

In one embodiment of the present disclosure, further blending of a cellulosic polymer and/or a zinc salt or a silver salt with an aqueous suspension agent comprising (E)-2-(7-trifluoromethylchroman-4-ylidene)-N-(7-hydroxy-5,6,7,8-tetrahydronaphthalen-1-yl)acetamide, or a pharmaceutically acceptable salt or solvate thereof, and a nonionic surfactant, can provide an aqueous suspension agent having improved redispersibility.

In one embodiment, it is possible to determine that the redispersibility is improved when the number of times of shaking required for the redispersion described above is typically about 15 times or less, preferably about 13 times or less, more preferably about 12 times or less, particularly preferably about 11 times or less, and further preferably about 10 times or less.

It is possible to consider that the measurement in the inversion operation reproduces the evaluation when used by patients who have weak hand strength due to some disorder or symptom and for which redispersing by shaking is difficult to perform, and thus, it is also possible to consider that the measurement evaluates the redispersibility during the use by such patients and the elderly.

In one embodiment, it is possible to determine that the redispersibility is improved when the number of times of the inversion operations required for the redispersion described above is typically about 40 times or less, preferably about 35 times or less, more preferably about 30 times or less, particularly preferably about 25 times or less, and further preferably about 20 times or less.

In one embodiment, redispersibility can be evaluated by any means, and redispersibility can also be evaluated by filling a container with the aqueous suspension of the present disclosure, performing a shaking operation at any speed and/or any shaking width, or an inversion operation, on the container, and measuring the number of times until the suspended particles are redispersed.

In one embodiment, (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, in the aqueous suspension of the present disclosure, has, without particular limitation, an average particle size $(D_{50})$ of typically from about 0.1 $\mu m$ to about 50 $\mu m$, preferably from about 0.5 $\mu m$ to about 10 $\mu m$, particularly preferably from about 1 $\mu m$ to about 10 $\mu m$, and still more preferably from about 1 $\mu m$ to about 5 $\mu m$. Setting the average particle size within such a range can improve the redispersibility.

In one embodiment, (E)-2-(7-trifluoromethylchroman-4-ylidene)-N-(7-hydroxy-5,6,7,8-tetrahydronaphthalen-1-yl) acetamide, or a pharmaceutically acceptable salt or solvate thereof, in the aqueous suspension of the present disclosure, can be used as a crystalline form. The crystal form is not particularly limited as long as it does not affect redispersibility. For example, in the present disclosure, it is possible to use the type I crystals, type II crystals, type III crystals, or a mixture thereof, of (E)-2-(7-trifluoromethylchroman-4-ylidene)-N-((7R)-7-hydroxy-5,6,7,8-tetrahydronaphthalen-1-yl)acetamide disclosed in International Publication No. WO 2018/221543 Pamphlet, Japanese Patent No. 6230743, and the like. The type I crystal is preferably used.

(Stability)

(E)-2-(7-trifluoromethylchroman-4-ylidene)-N-(7-hy-droxy-5,6,7,8-tetrahydronaphthalen-1-yl)acetamide, or a pharmaceutically acceptable salt or solvate thereof, has very low solubility in water. Therefore, in the aqueous suspension agent of the present disclosure, the (E)-2-(7-trifluorometh-ylchroman-4-ylidene)-N-(7-hydroxy-5,6,7,8-tetrahy-dronaphthalen-1-yl)acetamide, or the pharmaceutically acceptable salt or solvate thereof, becomes suspended par-ticles; however, some are dissolved in aqueous solutions. In one embodiment of the present disclosure, (E)-2-(7-trifluo-romethylchroman-4-ylidene)-N-(7-hydroxy-5,6,7,8-tetrahy-dronaphthalen-1-yl)acetamide, or a pharmaceutically acceptable salt or solvate thereof, is suspended in an aqueous solution containing tyloxapol so that decomposition of (E)-2-(7-trifluoromethylchroman-4-ylidene)-N-(7-hydroxy-5,6, 7,8-tetrahydronaphthalen-1-yl)acetamide, or the pharma-ceutically acceptable salt or solvate thereof, in an aqueous solution can be inhibited, thereby improving the stability of the aqueous suspension agent.

Accordingly, in other aspects of the present disclosure, a composition for improving the stability of (E)-2-(7-trifluo-romethylchroman-4-ylidene)-N-(7-hydroxy-5,6,7,8-tetrahy-dronaphthalen-1-yl)acetamide, or a pharmaceutically acceptable salt or solvate thereof, in an aqueous suspension agent can be provided, where the composition comprises tyloxapol.

In other aspects, a method of improving the stability of (E)-2-(7-trifluoromethylchroman-4-ylidene)-N-(7-hydroxy-5,6,7,8-tetrahydronaphthalen-1-yl)acetamide, or a pharma-ceutically acceptable salt or solvate thereof, in an aqueous suspension agent is provided, where the method comprises the step of mixing (E)-2-(7-trifluoromethylchroman-4-ylidene)-N-(7-hydroxy-5,6,7,8-tetrahydronaphthalen-1-yl) acetamide or a pharmaceutically acceptable salt or solvate thereof, and tyloxapol to prepare an aqueous suspension agent.

In one embodiment of the present disclosure, stability can be evaluated by the content retention rate (residual rate) of (E)-2-(7-trifluoromethylchroman-4-ylidene)-N-(7-hydroxy-5,6,7,8-tetrahydronaphthalen-1-yl)acetamide, or a pharma-ceutically acceptable salt or solvate thereof, dissolved and/or suspended in an aqueous suspension, after storage for a certain period of time. Thus, stability is preferably evaluated by dissolving (E)-2-(7-trifluoromethylchroman-4-ylidene)-N-(7-hydroxy-5,6,7,8-tetrahydronaphthalen-1-yl)acet-amide, or a pharmaceutically acceptable salt or solvate thereof, in an aqueous solution agent containing an exces-sive amount of nonionic surfactant and by using the content retention rate in the aqueous solution as an index.

Eye drops are administered directly to the mucous mem-brane of the eye. Thus, it is necessary to ensure a high level of safety of the eye drops, and it is necessary to suppress the generation of decomposition products therein during stor-age. In particular, in the development of pharmaceuticals for medical use, if the concentration of decomposition products generated by storage under prescribed conditions exceeds a certain amount, it is obligatory to specify the structure of the decomposition products and submit a safety report (PMSB/ELD Notification No. 0624001 "Regarding the revision of the guidelines for impurities in drug products containing new active ingredients"). In the development of eye drops, this obligation usually arises when the concentration of degradation products exceeds 1.0%. For this reason, it is necessary to sufficiently suppress the generation of decom-position products caused by storage in the formulation of eye drops. In addition, with regard to aqueous suspension agents in general, compounds in a dissolved state are more susceptible to stability than compounds in a solid state (suspended particles). It is thus important to evaluate sta-bility in the dissolved state from the viewpoint of drug quality control.

(Dosage Form)

In one embodiment of the present disclosure, the aqueous suspension agent is an ophthalmic suspension agent and may be provided as eye injections, eye drops, or eye irrigation solutions. For example, the ophthalmic suspension agent may be provided in the form of a suspension in which the active ingredient is suspended in an aqueous solvent (e.g., phosphate-buffered saline) or in the form of a solution in which the active ingredient is dissolved therein.

In one embodiment of the present disclosure, the aqueous suspension agent may be eye drops for treating dry eye. Dry eye is a disease accompanied by subjective symptoms such as eye discomfort, and requires long-term and regular treat-ment. In addition, since dry eye therapeutic drugs are generally administered in a large number of doses, formu-lations with good patient adherence and convenience are strongly desired. Furthermore, in the case of a suspension with poor redispersibility, there is concern that the sus-pended particles will not be uniformly dispersed, the desired active ingredient will not be administered, and the pharma-cological effect will not be sufficiently exhibited. From these points of view as well, redispersibility is a major issue in eye drops for treating dry eye, and the provision of an aqueous suspension agent having excellent redispersibility according to the present disclosure is highly valuable.

The aqueous suspension agent of the present disclosure can be administered by any suitable route determined by those of ordinary skill in the art, and the aqueous suspension agent may be formulated to be suitable for administration by a route of administration selected from, without particular limitation, ophthalmic injection, topical application (includ-ing application to the eye), eye drop, intravenous injection, infusion, oral, parenteral, transdermal, and the like.

ADDITIVES AND/OR EXCIPIENTS

The aqueous suspension agent of the present disclosure may comprise any pharmaceutically acceptable additives and/or excipients known in the art. Additives include, but are not limited to, stabilizers, pH adjusters, buffers, and preser-vatives (antiseptics).

The stabilizer is not particularly limited as long as it is pharmaceutically acceptable, and it includes, for example, polyvinylpyrrolidone, monoethanolamine, cyclodextrin, dextran, ascorbic acid, tocopherol, dibutylhydroxytoluene, sulfites and the like. The content thereof is preferably about 0.001 w/v % to about 1 w/v % relative to the total amount of the composition.

The pH adjuster is not particularly limited as long as it is pharmaceutically acceptable, and it includes, for example, acids, such as hydrochloric acid, acetic acid, boric acid, aminoethylsulfonic acid and epsilon-aminocaproic acid; alkalis, such as sodium hydroxide, potassium hydroxide, borax, triethanolamine, monoethanolamine, sodium hydro-gen carbonate and sodium carbonate, and the like. The content thereof is, for example, zero to about 20 w/v % relative to the total amount of the aqueous suspension agent.

In one embodiment of the present disclosure, the aqueous suspension of the present disclosure can optionally be mixed with a pH adjuster as described above so as to have a pH of typically from about 4 to about 8, preferably from about 5.0 to about 8.0, more preferably from about 6.0 to about 8.0, particularly preferably from about 7.0. to about 8.0, and still more preferably from about 7.2 to about 7.8.

The buffer used in the aqueous suspension agent of the present disclosure is not particularly limited as long as it is pharmaceutically acceptable, and it includes, for example, borate buffers, phosphate buffers, tris buffers, citrate buffers, tartrate buffers, acetate buffers, amino acid buffers, and the like. From the viewpoint of redispersibility or stability of the aqueous suspension agent, borate buffers or phosphate buffers are preferred, and borate buffers are particularly preferred.

The concentration of the buffering agent may be appropriately set within a range in which the desired buffering capacity can be imparted to the aqueous solution agent, and examples thereof include about 0.1 w/v % to about 10 w/v %. From the viewpoint of improving redispersibility or stability, it is preferably from about 1 w/v % to about 5 w/v %, and more preferably from about 1 w/v % to about 3 w/v %.

The borate buffer is not particularly limited as long as it is pharmaceutically acceptable, and it includes, for example, boric acid and/or salts thereof. Boric acid is not particularly limited as long as it is pharmaceutically acceptable, and it includes, for example, orthoboric acid, metaboric acid, and tetraboric acid. The salt of boric acid is not particularly limited as long as it is pharmaceutically acceptable, and it includes metal salts, such as sodium salts, potassium salts, calcium salts, magnesium salts and aluminum salts; organic amine salts, such as triethylamine, triethanolamine, morpholine, piperazine and pyrrolidine, and the like. Boric acid or a salt thereof may be used singly or in combination of two or more. In addition, a preferred mode of the borate buffer is a combination of boric acid and borax.

The ratio of boric acid and borax when using boric acid and borax in combination is not particularly limited. The ratio is, for example, 10 to 300 parts by mass, preferably 10 to 250 parts by mass, more preferably 30 to 100 parts by mass, and particularly preferably 40 to 60 parts by mass, per 100 parts by mass of boric acid.

The phosphate buffer specifically includes phosphoric acid and/or salts thereof. The salt of phosphoric acid is not particularly limited as long as it is pharmaceutically acceptable, and it includes, for example, dialkali metal salts of hydrogen phosphate such as disodium hydrogen phosphate and dipotassium hydrogen phosphate; dihydrogen phosphate alkali metal salts such as sodium dihydrogen phosphate and potassium dihydrogen phosphate; tribasic metal phosphates such as trisodium phosphate and tripotassium phosphate, and the like. In addition, the salt of phosphoric acid may be in the form of a solvate such as a hydrate. For example, in the case of disodium hydrogen phosphate, it may be in the form of a dodecahydrate; and in the case of sodium dihydrogen phosphate, it may be in the form of a dihydrate, or the like. As the phosphate buffer, one of phosphoric acid and salts thereof may be selected and used alone, or two or more thereof may be used in combination. Among phosphoric acid and salts thereof, phosphates are preferred, more preferably at least one of dialkali metal hydrogen phosphate and alkali metal dihydrogen phosphate, at least one of dialkali metal hydrogen phosphate and alkali metal dihydrogen phosphate is more preferred, and at least one of disodium hydrogen phosphate and sodium dihydrogen phosphate is particularly preferred.

The tris buffer includes tris (also known as trishydroxymethylaminomethane) and/or salts thereof. The tris salt is not particularly limited as long as it is pharmaceutically acceptable, and it includes, for example, salts such as acetate, hydrochloride, maleate, and sulfonate. As the tris buffer, one selected from tris and salts thereof may be used alone, or two or more thereof may be used in combination. In addition, in other embodiments, the tris buffer specifically includes trometamol and/or salts thereof. The salt of trometamol is not particularly limited as long as it is pharmaceutically acceptable, and it includes, for example, organic acid salts such as acetates; and inorganic acid salts such as hydrochlorides and sulfonates. As the tris buffer, one of trometamol and salts thereof may be selected and used alone, or two or more thereof may be used in combination. Among trometamol and salts thereof, trometamol is preferred.

The citric acid buffer specifically includes citric acid and/or salts thereof. The salt of citric acid is not particularly limited as long as it is pharmaceutically acceptable, and it includes, for example, alkali metal salts such as sodium salts and potassium salts; alkaline earth metal salts such as calcium salts and magnesium salts, and the like. In addition, the salt of citric acid may be in the form of a solvate such as a hydrate. As the citric acid buffer, one of citric acid and salts thereof may be selected and used alone, or two or more thereof may be used in combination. Among citric acid and salts thereof, citric acid salts are preferred, alkali metal citric acid salts are more preferred, and sodium citrate is particularly preferred.

The Tartaric acid buffer specifically includes tartaric acid and/or salts thereof. The salt of tartaric acid is not particularly limited as long as it is pharmaceutically acceptable, and it includes, for example, alkali metal salts such as sodium salts and potassium salts; alkaline earth metal salts such as calcium salts and magnesium salts, and the like. In addition, the salt of tartaric acid may be in the form of a solvate such as a hydrate. As the tartaric acid buffer, one of tartaric acid and salts thereof may be selected and used alone, or two or more thereof may be used in combination.

The acetate buffer specifically includes acetic acid and/or salts thereof. The salt of acetic acid is not particularly limited as long as it is pharmaceutically acceptable, and it includes, for example, alkali metal salts such as sodium salts and potassium salts; alkaline earth metal salts such as calcium salts and magnesium salts; ammonium salts, and the like. In addition, the salt of acetic acid may be in the form of a solvate such as a hydrate. As the acetate buffer, one of acetic acid and salts thereof may be selected and used alone, or two or more thereof may be used in combination.

The amino acid buffer specifically includes acidic amino acids and/or salts thereof. The acidic amino acid specifically includes aspartic acid and glutamic acid. The salt of acidic amino acid is not particularly limited as long as it is pharmaceutically acceptable, and it includes, for example, alkali metal salts such as sodium salts and potassium salts. As the amino acid buffer, one selected from acidic amino acids and salts thereof may be used alone, or two or more thereof may be used in combination.

The preservative is not particularly limited as long as it is pharmaceutically acceptable, and it includes, for example, sorbic acid, potassium sorbate, methyl parahydroxybenzoate, ethyl parahydroxybenzoate, propyl parahydroxybenzoate, butyl parahydroxybenzoate and other parahydroxybenzoic acid esters, chlorhexidine gluconate, benzalkonium chloride, benzethonium chloride, cetylpyridinium chloride and other quaternary ammonium salts, alkylpolyaminoethylglycine, chlorobutanol, polyquad, polyhexamethylene biguanide, chlorhexidine, and the like. The content thereof can be appropriately changed depending on the type thereof, and is, for example, about 0.0001 w/v % to about 0.2 w/v % relative to the total amount of the aqueous suspension agent.

Eye drops can be prepared, for example, by dissolving or suspending the above desired components in an aqueous solvent, such as sterilized purified water, physiological saline, or a buffer (e.g., phosphate buffer, citrate buffer, acetate buffer, etc.), or a non-aqueous solvent including vegetable oil such as cottonseed oil, soybean oil, sesame oil and peanut oil; adjusting the osmotic pressure to a predetermined level; and performing sterilization such as filtration sterilization.

(Container)

The container for containing the aqueous suspension agent of the present disclosure is not particularly limited, and examples thereof include glass containers and plastic containers. The plastic container may be made of any material such as polyester (polyethylene terephthalate, polyarylate), polycarbonate, polyethylene or polypropylene, mixtures thereof, and mixtures of these materials and others. The containers used in the present disclosure may be those used in the medical field or otherwise. In one embodiment, the container can be made of any material that can meet the "standard for plastic containers for eye drops" in the nation or other equivalent standards.

The shape of the container to be used may be any shape, and any shape can be used in general as long as it is a shape for eye drops.

In a certain embodiment, the aqueous suspension agent of the present disclosure can be filled into any eyedrop container commonly used in the medical field. For example, the aqueous suspension agent can be filled into polyethylene (preferably low density polyethylene) or polypropylene, preferably colorless polypropylene containers.

(General Techniques)

Molecular biological techniques, biochemical techniques, and microbiological techniques used herein are well known and commonly used in the art. For example, such techniques are described in Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (I996). Bioconjugate Techniques, Academic Press, Bessatsu Jikken Igaku "Gene transfer & expression analysis experimental method", YODOSHA CO., LTD., 1997, and the like. The relevant portions (may be all) of these are incorporated herein by reference.

Reference literatures such as scientific literatures, patents, and patent applications cited herein are incorporated herein by reference to the same extent that the entirety of each document is specifically described.

As described above, the present disclosure has been explained while showing preferred embodiments to facilitate understanding. The present disclosure is explained hereinafter based on Examples. The above explanation and the following Examples are not provided to limit the present disclosure, but for the sole purpose of exemplification. Thus, the scope of the present disclosure is not limited to the embodiments or the Examples specifically described herein and is limited only by the scope of claims.

EXAMPLES

Test Example 1: Change in Redispersibility in Accordance with Methylcellulose Concentration Preparation of Suspension A base solution was prepared according to the composition shown in Table 1, and Compound (1) was stirred and dispersed to obtain a suspension. Tyloxapol used was from AMRI Rensselaer (Curia Global, Inc.), and the methyl cellulose used was made by Shin-Etsu Chemical Co., Ltd. SM-15 was used as the methyl cellulose. For Compound (1), the above type I crystal was used.

Containment in the Container 5 mL each of the prepared suspension was sampled while stirring with a stirrer, and filled into an eye drop container. As the eye drop container, used was a colorless container consisting of polyethylene (container used for Gatiflo ophthalmic solution 0.3% (manufacturing and sales agency: Senju Pharmaceutical Co., Ltd.)).

Evaluation of Redispersibility

It was confirmed that the suspended particles in the suspension filled in the eye drop container were completely sedimented. One set consisted of 5 times of shaking, and the shaking operation was repeated until precipitate disappeared from the bottom surface and wall surface of the eyedrop container. The shaking operation was carried out with a width of 10 to 15 cm up and down, one shaking from shaking down to returning to the original position, and a speed of 1.1 seconds/set. The test was conducted with 3 to 5 specimens per formulation, and the average number of sets was obtained from the number of sets required for redispersion for each specimen, and converted to the number of times of shaking. When the number of times of shaking was 15 times or less, redispersion was determined to be favorable (examples: 5 shaking times for 1 set, 10 shaking times for 2 sets).

Measurement of Particle Size

The sample was shaken until the precipitate was redispersed, and then about 1 mL of the sample was dropped into the dispersing tank of a laser diffraction particle size distribution analyzer (SALD-2300). After performing ultrasonic treatment for 2 minutes, the particle size distribution was measured, and the value of the median diameter ($D_{50}$) was taken as the particle diameter.

Measurement of Surface Tension

The sample was shaken until the precipitate was redispersed, and then about 10 mL was added dropwise to a glass petri dish. The petri dish was set on a surface tensiometer, and the surface tension was measured by the plate method.

Test Results

Table 1 shows the results. At methylcellulose concentrations of 0.0001 w/v % to 0.005 w/v %, the number of times of shaking was 15 times or less. When 0.001 w/v % methylcellulose was added, the number of times of shaking was the least, which was 8.3 times. Note that the surface tension of the separately prepared base (formulation excluding Compound (1) and tyloxapol) was 54.6 mN/m, and there was no correlation between the redispersibility and the surface tension.

for redispersion was determined in the same manner as in Test Example 1. Hydroxypropyl methylcellulose (HPMC) used was manufactured by Shin-Etsu Chemical Co., Ltd., and Carboxymethyl cellulose (CMC) used was manufactured by DKS Co. Ltd. 60SH-4000 was used as hydroxypropylmethylcellulose, and Celogen PR-S was used as carboxymethylcellulose. For Compound (1), the above type I crystal was used.

TABLE 1

| component (g/100 mL) | Formulation 1 | Formulation 2 | Formulation 3 | Formulation 4 | Formulation 5 | Formulation 6 |
|---|---|---|---|---|---|---|
| Compound (1) | 1.0 g | 1.0 g | 1.0 g | 1.0 g | 1.0 g | 1.0 g |
| boric acid | 1.64 g | 1.64 g | 1.64 g | 1.64 g | 1.64 g | 1.64 g |
| borax | 0.54 g | 0.54 g | 0.54 g | 0.54 g | 0.54 g | 0.54 g |
| tyloxapol | 0.01 g | 0.01 g | 0.01 g | 0.01 g | 0.01 g | 0.01 g |
| methylcellulose | 0.1 g | 0.05 g | 0.01 g | 0.005 g | 0.003 g | 0.001 g |
| purified water | proper quantity | proper quantity | proper quantity | proper quantity | proper quantity | proper quantity |
| total amount | 100 mL | 100 mL | 100 mL | 100 mL | 100 mL | 100 mL |
| pH | 7.5 | 7.5 | 7.5 | 7.5 | 7.5 | 7.5 |
| osmotic pressure ratio | 1.0 | 1.0 | 1.0 | 1.0 | 1.0 | 1.0 |
| particle diameter ($D_{50}$, μm) | 2.66 | 2.61 | 2.67 | 2.78 | — | — |
| surface tension (mN/m) | 41.92 | — | 39.67 | 38.43 | — | 39.13 |
| redispersibility evaluation (number of shaking) | 23.3 | 21.7 | 20.0 | 15.0 | 11.7 | 8.3 |

| component (g/100 mL) | Formulation 7 | Formulation 8 | Formulation 9 | Formulation 10 | Formulation 11 |
|---|---|---|---|---|---|
| Compound (1) | 1.0 g | 1.0 g | 1.0 g | 1.0 g | 1.0 g |
| boric acid | 1.66 g | 1.64 g | 1.64 g | 1.64 g | 1.64 g |
| borax | 0.54 g | 0.54 g | 0.54 g | 0.54 g | 0.54 g |
| tyloxapol | 0.01 g | 0.01 g | 0.01 g | 0.01 g | 0.01 g |
| methylcellulose | 0.0007 g | 0.0005 g | 0.0001 g | 0.00005 g | 0.00001 g |
| purified water | proper quantity | proper quantity | proper quantity | proper quantity | proper quantity |
| total amount | 100 mL | 100 mL | 100 mL | 100 mL | 100 mL |
| pH | 7.5 | 7.5 | 7.5 | 7.5 | 7.5 |
| osmotic pressure ratio | 1.0 | 1.0 | 1.0 | 1.0 | 1.0 |
| particle diameter ($D_{50}$, μm) | 2.45 | 2.59 | 2.58 | 2.56 | 2.55 |
| surface tension (mN/m) | — | — | 39.27 | — | 40.43 |
| redispersibility evaluation (number of shaking) | 10.0 | 11.7 | 15.0 | 20.0 | 21.7 |

Test Example 2: Comparative Study of Cellulose Derivatives

A suspension having the composition shown in Table 2 was prepared, and the number of times of shaking required Test Results Table 2 shows the results. By adding 0.0005 w/v % to 0.003 w/v % HPMC, the number of times of shaking became 15 times or less. When 0.001 w/v % HPMC was blended, the number of times of shaking was the lowest, which was 11.7 times. By blending 0.001 w/v % CMC, the number of times of shaking was 11.7 times.

TABLE 2

| component (g/100 mL) | Formulation 12 | Formulation 13 | Formulation 14 | Formulation 15 | Formulation 16 |
|---|---|---|---|---|---|
| Compound (1) | 1.0 g | 1.0 g | 1.0 g | 1.0 g | 1.0 g |
| boric acid | 1.64 g | 1.64 g | 1.64 g | 1.64 g | 1.64 g |
| borax | 0.54 g | 0.54 g | 0.54 g | 0.54 g | 0.54 g |
| tyloxapol | 0.01 g | 0.01 g | 0.01 g | 0.01 g | 0.01 g |
| HPMC | 0.1 g | 0.01 g | 0.003 g | 0.001 g | 0.0005 g |
| CMC | — | — | — | — | — |
| purified water | proper quantity | proper quantity | proper quantity | proper quantity | proper quantity |

TABLE 2-continued

| | | | | | |
|---|---|---|---|---|---|
| total amount | 100 mL | 100 mL | 100 mL | 100 mL | 100 mL |
| pH | 7.5 | 7.5 | 7.5 | 7.5 | 7.5 |
| osmotic pressure ratio | 1.0 | 1.0 | 1.0 | 1.0 | 1.0 |
| redispersibility evaluation (number of shaking) | 30.0 | 23.3 | 15.0 | 11.7 | 13.3 |

| component (g/100 mL) | Formulation 17 | Formulation 18 | Formulation 19 | Formulation 20 | Formulation 21 |
|---|---|---|---|---|---|
| Compound (1) | 1.0 g | 1.0 g | 1.0 g | 1.0 g | 1.0 g |
| boric acid | 1.64 g | 1.64 g | 1.64 g | 1.64 g | 1.64 g |
| borax | 0.54 g | 0.54 g | 0.54 g | 0.54 g | 0.54 g |
| tyloxapol | 0.01 g | 0.01 g | 0.01 g | 0.01 g | 0.01 g |
| HPMC | 0.00005 g | 0.00001 g | — | — | — |
| CMC | — | — | 0.01 | 0.001 | 0.00001 |
| purified water | proper quantity | proper quantity | proper quantity | proper quantity | proper quantity |
| total amount | 100 mL | 100 mL | 100 mL | 100 mL | 100 mL |
| pH | 7.5 | 7.5 | 7.5 | 7.5 | 7.5 |
| osmotic pressure ratio | 1.0 | 1.0 | 1.0 | 1.0 | 1.0 |
| redispersibility evaluation (number of shaking) | 23.3 | 26.7 | 26.7 | 11.7 | 30.0 |

Test Example 3: Comparative Study of Nonionic Surfactants

A suspension having the composition shown in Table 3 was prepared, and the number of times of shaking required for redispersion was determined in the same manner as in Test Example 1. Polysorbate 80 used was manufactured by NOF Corporation. Polyethylene glycol 40 monostearate (MYS-40) used was manufactured by Nippon Surfactant Industries Co., Ltd. For Compound (1), the above type I crystal was used.

Test Results

Table 3 shows the results. As for the suspensions with tyloxapol, polysorbate 80, and MYS-40 added therein, the number of times of shaking became 15 times or less.

TABLE 3

| component (g/100 mL) | Formulation 22 | Formulation 23 | Formulation 24 |
|---|---|---|---|
| Compound (1) | 1.0 g | 1.0 g | 1.0 g |
| boric acid | 1.59 g | 1.59 g | 1.58 g |
| borax | 0.48 g | 0.48 g | 0.48 g |
| MC | 0.001 g | 0.001 g | 0.001 g |
| tyloxapol | 0.02 g | — | — |
| polysorbate 80 | — | 0.02 g | — |
| MYS-40 | — | — | 0.02 g |
| purified water | proper quantity | proper quantity | proper quantity |
| total amount | 100 mL | 100 mL | 100 mL |
| pH | 7.5 | 7.5 | 7.5 |
| osmotic pressure | 1.0 | 1.0 | 1.0 |
| redispersibility evaluation (number of shaking) | 10.0 | 13.3 | 11.7 |

Test Example 4: Comparative Examination of Water-Soluble Polymers Other than Cellulose A suspension having the composition shown in Table 4 was prepared, and the number of times of shaking required for redispersion was determined in the same manner as in Test Example 1. Polyvinylpyrrolidone (PVP) used was made by BASF Japan. The xanthan gum used was manufactured by DSP Gokyo Food & Chemical Co., Ltd. Carboxyvinyl polymer (CVP) used was manufactured by Lubrizol. Note that Kollidon 30 was used as polyvinylpyrrolidone, and 974P was used as carboxyvinyl polymer. For Compound (1), the above type I crystal was used.

Test Results

Table 4 shows the results. The number of times of shaking of the suspension with PVP, xanthan gum, and CVP blended therein was 15 times or more.

TABLE 4

| component (g/100 mL) | Formulation 25 | Formulation 26 | Formulation 27 |
|---|---|---|---|
| Compound (1) | 1.0 g | 1.0 g | 1.0 g |
| boric acid | 1.64 g | 1.64 g | 1.64 g |
| borax | 0.54 g | 0.54 g | 0.54 g |
| tyloxapol | 0.01 g | 0.01 g | 0.01 g |
| PVP | 0.001 g | — | — |
| xanthan gum | — | 0.001 g | — |
| CVP | — | — | 0.001 g |
| purified water | proper quantity | proper quantity | proper quantity |
| total amount | 100 mL | 100 mL | 100 mL |
| pH | 7.5 | 7.5 | 7.5 |
| osmotic pressure ratio | 1.0 | 1.0 | 1.0 |
| redispersibility evaluation (number of shaking) | 21.7 | 25.0 | 28.3 |

Test Example 5: Change in Redispersibility Due to Addition of Zinc Chloride

A suspension having the composition shown in Table 5 was prepared and filled into an eyedrop container. Zinc chloride made by Merck KGaA was used. For Compound (1), the above type I crystal was used.

Evaluation of Redispersibility

It was confirmed that the suspended particles in the suspension filled in the eye drop container were completely sedimented. The inversion operation was performed, and this operation was repeated until the precipitate disappeared from the bottom surface and wall surface of the eye drop container and was redispersed. The number of inversion operations required until redispersion was counted. The test was conducted with 3 to 5 specimens per formulation, and the average number of inversion operations was calculated.

Test Results

Table 5 shows the results. When methylcellulose was added to the formulation of Formulation 28, the number of inversion operations changed from 47.3 times to 24.7 times. When zinc chloride was added to the formulation of Formula 28, the number of inversion operations was 32.3 times. When methyl cellulose and zinc chloride were added together, the number of inversion operations was 16.0 times.

TABLE 5

| component (g/100 mL) | Formulation 28 | Formulation 29 | Formulation 30 | Formulation 31 |
|---|---|---|---|---|
| Compound (1) | 1.0 g | 1.0 g | 1.0 g | 1.0 g |
| boric acid | 1.64 g | 1.64 g | 1.64 g | 1.64 g |
| borax | 0.54 g | 0.54 g | 0.54 g | 0.54 g |
| tyloxapol | 0.03 g | 0.03 g | 0.03 g | 0.03 g |
| methylcellulose | — | 0.001 g | — | 0.001 |
| zinc chloride | — | — | 0.002 g | 0.002 g |
| purified water | proper quantity | proper quantity | proper quantity | proper quantity |
| total amount | 100 mL | 100 mL | 100 mL | 100 mL |
| pH | 7.5 | 7.5 | 7.5 | 7.5 |
| osmotic pressure ratio | 1.0 | 1.0 | 1.0 | 1.0 |
| redispersibility evaluation (number of inversion operation) | 47.3 | 24.7 | 32.3 | 16.0 |

Test Example 6: Stability of Compound (1) in Nonionic Surfactant Solution

Preparation of Aqueous Solution

A base solution was prepared according to the composition shown in Table 6, and Compound (1) was dissolved therein to obtain an aqueous solution. Each 2 mL of the prepared aqueous solution was sampled and filled into a glass ampoule. Tyloxapol used was manufactured by Ruger. For Compound (1), the above type I crystal was used.

Evaluation of Stability

The aqueous solution was stored at 25° C. for 1 month (1M), and the content of compound (1) in the solution was measured using a liquid chromatography device (manufactured by Shimadzu Corporation) under the conditions below. The content retention rate was determined as the ratio (%) of the measured content after storage to the amount of Compound (1) used for preparation.

(Measurement Conditions)

Column: X Bridge Phenyl 3.5 µm, 4.6×150 mm, 3.5 µm (Waters)

Detector: UV-visible spectrophotometric detector

Detection wavelength: 220 nm

Column temperature: 40° C.

Mobile phase: water/acetonitrile/trifluoroacetic acid mixture (50:50:0.02)

Measurement Result

Table 6 shows the results. The content retention rate of compound (1) after 1M storage at 25° C. was 100%, and Compound (1) was stable in an aqueous solution containing tyloxapol.

TABLE 6

| component (g/100 mL) | Formulation 32 |
|---|---|
| Compound (1) | 0.001 g |
| disodium hydrogen phosphate | 0.165 g |
| sodium dihydrogen phosphate | 0.046 g |
| tyloxapol | 1.0 g |
| purified water | proper quantity |
| total amount | 100 mL |
| pH | 7.0 |
| content retention rate (to display ratio %) | 100 |

Test Example 7: Change in Redispersibility Due to Addition of Each Metal

Suspensions having the compositions shown in Tables 7 to 9 were prepared, and the number of inversion operations required for redispersion was determined in the same manner as in Test Example 5. Zinc sulfate used was from Merck KGaA. The silver nitrate used was manufactured by Fuji Film Wako Pure Chemical Corporation. Sodium chloride used was manufactured by Manac. Potassium chloride used was manufactured by Manac. Calcium chloride used was manufactured by Fuji Film Wako Pure Chemical Corporation. Magnesium chloride used was manufactured by Nacalai Tesque. For Compound (1), the above type I crystal was used.

TABLE 7

| component (g/100 mL) | Formulation 33 | Formulation 34 | Formulation 35 |
|---|---|---|---|
| Compound (1) | 1.0 | 1.0 | 1.0 |
| boric acid | 1.64 | 1.64 | 1.64 |
| borax | 0.54 | 0.54 | 0.54 |
| tyloxapol | 0.03 | 0.03 | 0.03 |
| zinc chloride | 0.01 | 0.005 | 0.0005 |
| purified water | proper quantity | proper quantity | proper quantity |
| total amount | 100 mL | 100 mL | 100 mL |
| pH | 7.5 | 7.5 | 7.5 |
| osmotic pressure ratio | 1.0 | 1.0 | 1.0 |
| redispersibility evaluation (number of inversion operation) | 31.3 | 33.3 | 34.7 |

TABLE 8

| component (g/100 mL) | Formulation 36 | Formulation 37 | Formulation 38 |
|---|---|---|---|
| Compound (1) | 1.0 | 1.0 | 1.0 |
| boric acid | 1.64 | 1.64 | 1.64 |
| borax | 0.54 | 0.54 | 0.54 |
| tyloxapol | 0.03 | 0.03 | 0.03 |
| methylcellulose | — | 0.001 | — |
| zinc sulfate | 0.001 | 0.001 | — |
| silver nitrate | — | — | 0.002 |
| purified water | proper quantity | proper quantity | proper quantity |
| total amount | 100 mL | 100 mL | 100 mL |
| pH | 7.5 | 7.5 | 7.5 |
| osmotic pressure ratio | 1.0 | 1.0 | 1.0 |
| redispersibility evaluation (number of inversion operation) | 32.3 | 16.3 | 31.3 |

TABLE 9

| component (g/100 mL) | Comparison 1 | Comparison 2 | Comparison 3 | Comparison 4 |
|---|---|---|---|---|
| Compound (1) | 1.0 | 1.0 | 1.0 | 1.0 |
| boric acid | 1.64 | 1.64 | 1.64 | 1.64 |
| borax | 0.54 | 0.54 | 0.54 | 0.54 |
| tyloxapol | 0.03 | 0.03 | 0.03 | 0.03 |
| sodium chloride | 0.002 | — | — | — |
| potassium chloride | — | 0.002 | — | — |
| calcium chloride | — | — | 0.002 | — |
| magnesium chloride | — | — | — | 0.002 |
| purified water | proper quantity | proper quantity | proper quantity | proper quantity |
| total amount | 100 mL | 100 mL | 100 mL | 100 mL |
| pH | 7.5 | 7.5 | 7.5 | 7.5 |
| osmotic pressure ratio | 1.0 | 1.0 | 1.0 | 1.0 |
| redispersibility evaluation (number of inversion operation) | 45.7 | 46.0 | 46.3 | 44.7 |

Tables 7 to 9 show the results. Favorable redispersibility was exhibited by blending 0.0005 w/v to 0.01 w/v of zinc chloride. Further, favorable redispersibility was also exhibited when zinc sulfate or silver nitrate was added. On the other hand, no favorable redispersibility was exhibited when sodium chloride, potassium chloride, calcium chloride, or magnesium chloride was blended.

Test Example 8: Change in Redispersibility of 0.3 w/v % Compound (1)

A suspension having the composition shown in Table 10 was prepared, and the number of times of shaking required for redispersion was determined in the same manner as in Test Example 1.

TABLE 10

| component (g/100 mL) | Formulation 39 | Formulation 40 | Formulation 41 | Formulation 42 | Formulation 43 |
|---|---|---|---|---|---|
| Compound (1) | 0.3 | 0.3 | 0.3 | 0.3 | 0.3 |
| boric acid | 1.64 | 1.64 | 1.64 | 1.64 | 1.64 |
| borax | 0.54 | 0.54 | 0.54 | 0.54 | 0.54 |
| tyloxapol | 0.05 | 0.05 | 0.05 | 0.05 | 0.05 |
| methylcellulose | 0.1 | 0.003 | 0.001 | 0.0005 | 0.00001 |
| purified water | proper quantity | proper quantity | proper quantity | proper quantity | proper quantity |
| total amount | 100 mL | 100 mL | 100 mL | 100 mL | 100 mL |
| pH | 7.5 | 7.5 | 7.5 | 7.5 | 7.5 |
| osmotic pressure ratio | 1.0 | 1.0 | 1.0 | 1.0 | 1.0 |
| redispersibility evaluation (number of shaking) | 16.7 | 11.7 | 6.7 | 10.0 | 18.3 |

At a methylcellulose concentration of 0.0005 w/v % to 0.003 w/v %, the number of times of shaking was 15 times or less. When 0.001 w/v % methylcellulose was added, the number of times of shaking was the least, which was 6.7 times. In addition, when 0.001 w/v % methyl cellulose was added and redispersibility was evaluated by the inversion operation, it was 17.0 times with Formulation 6 while it was 12.7 times with Formulation 41 (not shown in the table). As such, favorable redispersibility was also confirmed by the number of inversion operations.

Test Example 9: Change in Redispersibility Due to Addition of Zinc Chloride

A suspension having the composition shown in Table 11 was prepared, and the number of inversion operations required for redispersion was determined in the same manner as in Test Example 5.

TABLE 11

| component (g/100 mL) | Formulation 44 | Formulation 45 | Formulation 46 |
|---|---|---|---|
| Compound (1) | 0.3 | 0.3 | 0.3 |
| boric acid | 1.64 | 1.64 | 1.64 |
| borax | 0.54 | 0.54 | 0.54 |
| tyloxapol | 0.05 | 0.05 | 0.05 |
| methylcellulose | — | — | 0.001 |
| zinc chloride | — | 0.002 | 0.002 |
| purified water | proper quantity | proper quantity | proper quantity |
| total amount | 100 mL | 100 mL | 100 mL |
| pH | 7.5 | 7.5 | 7.5 |
| osmotic pressure ratio | 1.0 | 1.0 | 1.0 |
| redispersibility evaluation (number of inversion operation) | 40.7 | 23.0 | 11.3 |

When zinc chloride was added to the formulation of Formula 44, the number of inversion operations changed from 40.7 times to 23.0 times. When methylcellulose and zinc chloride were added together, the number of inversion operations was 11.3 times. Further, when the redispersibility was evaluated by the number of shaking when both methylcellulose and zinc chloride were added, the number of shaking was 5.0 times (not shown in the table). As such, favorable redispersibility was also confirmed by the number of inversion operations.

Manufacturing Example

High-quality eye drops can be manufactured by preparing aqueous suspension agents having the compositions shown in Tables 12 to 14. In addition, the prescription amount of Compound (1) and each additive is described as "g/100 mL."

TABLE 12

| | Eye Drop No. | 1 | 2 | 3 | 4 | 5 | 6 | 7 | 8 |
|---|---|---|---|---|---|---|---|---|---|
| ophthalmic solution | Compound (1) | 0.3 | 1.0 | 0.3 | 0.3 | 0.3 | 0.3 | 0.3 | 1.0 |
| | baric acid | 1.64 | 1.64 | 1.4 | | 1.62 | 1.62 | 1.4 | |
| | borax | 0.54 | 0.54 | 0.35 | | 0.52 | 0.52 | 0.35 | |
| | disodium hydrogen phosphate hydrate | | | | 0.165 | | | | 0.165 |
| | sodium dihydrogen phosphate hydrate | | | | 0.046 | | | | 0.046 |
| | tyloxapol | 0.03 | 0.03 | 0.01 | 0.01 | | 0.01 | 0.05 | 0.05 |
| | polysorbate 80 | | | | | 0.01 | | | |
| | methylcellulose | 0.0005 | | | 0.0007 | | | | |
| | hydroxypropylmethylcellulose | | 0.0005 | | | 0.0007 | | 0.002 | |
| | carboxymethylcellulose | | | 0.0005 | | | 0.0007 | | 0,002 |
| | zinc chloride | 0.0005 | 0.0005 | | | 0.0005 | 0.0005 | | |
| | silver nitrate | | | 0.002 | 0.002 | | | 0.003 | 0.003 |
| | sodium chloride | | | 0.2 | 0.8 | | | 0.2 | |
| | sodium hydroxide | | | | proper quantity | | | | proper quantity |
| | purified water | proper quantity | proper quantity | proper quantity | proper quantity | proper quantity | proper quantity | proper quantity | proper quantity |
| | total amount | 100 mL | 100 mL | 100 mL | 100 mL | 100 mL | 100 mL | 100 mL | 100 mL |
| | pH | 7.5 | 7.5 | 7.5 | 7.5 | 7.5 | 7.5 | 7.5 | 7.5 |
| | osmotic pressure ratio | 1 | 1 | 1 | 1 | 1 | 1 | 1 | 1 |
| | particle diameter D50 (μm) | 2~4 | 2~4 | 2~4 | 2~4 | 2~4 | 2~4 | 2~4 | 2~4 |
| container | bottle | color-less PE | color-less PP | brown PE | color-less PE | color-less PP | brown PE | color-less PP | color-less PE |
| | sterilization method | EOG | EOG | EOG | EOG | EB | EB | EB | EB |

TABLE 13

| | Eye Drop No. | 9 | 10 | 11 | 12 | 13 | 14 | 15 | 16 |
|---|---|---|---|---|---|---|---|---|---|
| ophthalmic solution | Compound (1) | 1.0 | 0.3 | 0.3 | 0.3 | 0.3 | 0.3 | 9.3 | 0.3 |
| | baric acid | 1.64 | 1.64 | 1.4 | 1.64 | 1.62 | 1.62 | 1.64 | 1.4 |
| | borax | 0.54 | 0.54 | 0.35 | 0.54 | 0.52 | 0.52 | 0.54 | 0.35 |
| | tyloxapol | 0.01 | 0.03 | 0.03 | 0.01 | 0.01 | 0.01 | 0.01 | 0.01 |
| | methylcellulose | 0.003 | 0.0007 | 0.0007 | | 0.001 | 0.001 | | 0.001 |
| | hydroxypropylmethylcellulose | | | | 0.001 | | | 0.001 | |
| | zine chloride | 0.003 | | 0.003 | 0.002 | 0.002 | 0.002 | | 0.002 |
| | sodium chloride | | | 0.2 | | | | | 0.2 |
| | chlorhexidine gluconate | | | | | | 0.006 | 0.006 | |
| | purified water | proper quantity | proper quantity | proper quantity | proper quantity | proper quantity | proper quantity | proper quantity | proper quantity |
| | total amount | 100 mL | 100 mL | 100 mL | 100 mL | 100 mL | 100 mL | 100 mL | 100 mL |
| | pH | 7.5 | 7.5 | 7.5 | 7.5 | 7.5 | 7.5 | 7.5 | 7.5 |
| | osmatic pressure ratio | 1 | 3 | 1 | 1 | 1 | 1 | 1 | 1 |
| | particle diameter D50 (μm) | 2~4 | 2~4 | 2~4 | 2~4 | 2~4 | 2~4 | 2~4 | 2~4 |
| container | bottle | color-less PE | color-less PP | brown PE | color-less PE | color-less PP | brown PE | color-less PP | color-less PE |
| | sterilization method | EOG | EOG | EOG | EB | EB | EB | γ ray | VHP |

TABLE 14

| | | Eye Drop No. | | | |
|---|---|---|---|---|---|
| | | 17 | 18 | 19 | 20 |
| ophthalmic solution | Compound (1) | 0.3 | 0.3 | 1.0 | 0.3 |
| | boric acid | 1.64 | 1.64 | 1.62 | |
| | borax | 0.54 | 0.54 | 0.52 | |
| | disodium hydrogen phosphate hydrate | | | | 0.165 |
| | sodium dihydrogen phosphate hydrate | | | | 0.046 |
| | tyloxapol | 0.05 | 0.01 | 0.01 | 0.01 |
| | methylcellulose | | 0.001 | | |
| | zinc chloride | | 0.002 | | |
| | sodium chloride | | | | 0.8 |
| | Lifitegrast | 5.0 | 5.0 | 5.0 | 5.0 |
| | purified water | proper quantity | proper quantity | proper quantity | proper quantity |

TABLE 14-continued

| | | Eye Drop No. | | | |
| | | 17 | 18 | 19 | 20 |
| --- | --- | --- | --- | --- | --- |
| | total amount | 100 mL | 100 mL | 100 mL | 100 mL |
| | pH | 7.5 | 7.5 | 7.5 | 7.5 |
| | osmotic pressure ratio | 1 | 1 | 1 | 1 |
| | particle diameter D50 (μm) | 2~4 | 2~4 | 2~4 | 2~4 |
| container | bottle | colorless PP | colorless PP | brown PE | colorless PP |
| | sterilization method | EB | EB | EOG | VHP |

Tyloxapol (cloud point: 90 to 100° C.) is from AMRI Rensselaer (Curia Global, Inc.). Metlose SM-15 manufactured by Shin-Etsu Chemical Co., Ltd. is used as methyl cellulose. Hydroxypropyl methylcellulose (HPMC) used is Shin-Etsu Chemical 60SH-4000. Carboxymethyl cellulose (CMC) used is Celogen PR-S manufactured by DKS Co. Ltd. Lifitegrast used is manufactured by Shanghai Sumway Pharmaceutical Technology. For Compound (1), the above type I crystal is used.

Specifications of Respective Containers

Each container is constituted of a bottle (colorless PE, colorless PP or brown PP), a nozzle (PE), and a cap (PP). The appearance, brightness, chromaticity, saturation, and transmittance at each wavelength of the bottle body of each container are as specified in Table 15 and FIG. 1. Also, each container is shrink-wrapped as a product label.

EOG (ethylene oxide gas sterilization): The eye drop bottle is sterilized under conditions of ethylene oxide concentration of 400-700 mg/L, temperature of 40-50° C., relative humidity of 45-85%, and treatment time of 3 hours or longer.

VHP (hydrogen peroxide gas sterilization: Vaporous Hydrogen Peroxide): The eye drop bottle is sterilized under conditions of 3% VHP spray, temperature of 20-50° C., relative humidity of 30-90%, and treatment time of about 1 hour.

γ-ray (γ-ray sterilization): The bottle is sterilized by irradiation with 20-60 kGy of gamma rays.

50 L Scale Manufacture Method for Eye Drops (No. 11)

Purified water and predetermined amounts of boric acid, borax, sodium chloride and zinc chloride are put into a 30 L stainless steel container and stirred. A predetermined amount

TABLE 15

| | | | brightness | chromaticity | | | |
| bottle | material | appearance | L* | a* | b* | saturation | transmittence |
| --- | --- | --- | --- | --- | --- | --- | --- |
| colorless PE | polyethylene | colorless (white) | 69.39 | 1.54 | 13.83 | 13.92 | FIG. 1 |
| colorless PP | polypropylene | colorless (white) | 90.90 | 0.07 | 5.20 | 5.20 | FIG. 1 |
| brown PE | polyethylene | brown | 67.33 | 1.15 | 27.57 | 27.59 | FIG. 1 |

Bottle Shape

The bottle dimensions are about 23 m×about 17 mm×about 50 mm and the resin weight is about 3 g. The shape thereof is similar to the bottle of Softia® Eye Drops 0.02% (Manufacturing and sales agency: Senju Pharmaceutical Co., Ltd.).

Bottle Material

Polyethylene is low density polyethylene. Polypropylene is a propylene-ethylene copolymer having a propylene component/ethylene component ratio of 50/50 to 99.9/0.1, and it is similar to the bottle material of Softia® Eye Drops 0.02% (Manufacturing and sales agency: Senju Pharmaceutical Co., Ltd.).

Methods for Measuring the Brightness, Saturation, and Transmittance of Bottle Body Using a spectrophotometer (CM-5, manufactured by Konica Minolta Co., Ltd.), the brightness (L* value) and chromaticity (a* value, b* value) are measured for the side part (wide side part: 1.0 cm×2.0 to 3.0 cm) cut from the body of the bottle. Furthermore, saturation (c* value) was calculated according to the formula: $((a* \text{ value})^2+(b* \text{ value})^2)^{1/2}$. Furthermore, with regard to this side part, a UV-visible spectrophotometer ("UV-2450", manufactured by Shimadzu Corporation) is used to measure the transmittance (%) of light in the region of 200-800 nm.

Bottle Sterilization Method

EB (electron beam irradiation sterilization): The eye drop bottle is sterilized by electron beam irradiation at 10-60 kGy.

of tyloxapol aqueous solution is prepared in a 1 L stainless container, and this aqueous solution is put into a 30 L stainless container. Furthermore, after dispersing a predetermined amount of methyl cellulose with hot water (50 to 90° C.) in another 1 L stainless steel container, it is cooled, and this methyl cellulose aqueous solution is put into a 30 L stainless steel container. After confirming that all the additives have dissolved in a 30 L stainless steel container, purified water is added so as to obtain a base solution having a concentration of 1.5 times, and the weight is adjusted to a volume. This base solution is sterilized by filtration, and weighted up with purified water (including washing) to prepare a predetermined amount of base solution. Compound (1) is added to this base solution and dispersed by stirring to prepare a suspension. After confirming that the Compound (1) is dispersed in the liquid, the suspension is gently stirred for defoaming. Thereafter, the suspension is roughly filtered through a filter with a pore size of 75 μm, and the suspension is filled into a bottle while being stirred, and then the bottle is fitted with a nozzle and a cap.

NOTE

As described above, the present disclosure has been illustrated using the preferred embodiments of the present disclosure; however, it is understood that the scope of the present disclosure should be interpreted only by the Claims thereof. It is understood that the contents of patents, patent applications and documents cited herein should be incorporated herein by reference in the same way that the contents themselves thereof are specifically described herein. The present application claims priority to Japanese Patent Application No. 2021-57713 (filed on Mar. 30, 2021) filed with the Japan Patent Office, the contents of which are incorporated herein by reference in the same manner as all of them are described in the present specification.

INDUSTRIAL APPLICABILITY

The present disclosure can be used in fields such as medicine, pharmaceuticals, healthcare, biology, and biochemistry.

The invention claimed is:

1. An aqueous suspension agent comprising (a) (E)-2-(7-trifluoromethylchroman-4-ylidene)-N-(7-hydroxy-5,6,7,8-tetrahydronaphthalen-1-yl)acetamide or a pharmaceutically acceptable salt or solvate thereof, (b) a nonionic surfactant, (c) zinc chloride, and (d) water.

2. The aqueous suspension agent of claim 1, wherein the concentration of the nonionic surfactant in the aqueous suspension agent is from about 0.0001 w/v % to about 0.5 w/v %.

3. The aqueous suspension agent of claim 1, wherein the concentration of the nonionic surfactant in the aqueous suspension agent is from about 0.0001 w/v % to about 0.1 w/v %.

4. The aqueous suspension agent of claim 1, wherein the nonionic surfactant is at least one selected from the group consisting of tyloxapol, polysorbate 80, polyethylene glycol monostearate, and polyoxyethylene hydrogenated castor oil.

5. The aqueous suspension of claim 1, wherein the concentration of the (E)-2-(7-trifluoromethylchroman-4-ylidene)-N-(7-hydroxy-5,6,7,8-tetrahydronaphthalen-1-yl) acetamide or the pharmaceutically acceptable salt or solvate thereof in the aqueous suspension agent is from about 0.01% w/v to about 5% w/v.

6. The aqueous suspension agent of claim 1, wherein the concentration of zinc chloride in the aqueous suspension agent is from about 0.0001 w/v % to about 0.05 w/v %.

7. The aqueous suspension agent of claim 1, wherein the (E)-2-(7-trifluoromethylchroman-4-ylidene)-N-(7-hydroxy-5,6,7,8-tetrahydronaphthalen-1-yl)acetamide is (E)-2-(7-trifluoromethylchroman-4-ylidene)-N-((7R)-7-hydroxy-5,6,7,8-tetrahydronaphthalen-1-yl)acetamide.

8. The aqueous suspension agent of claim 1, further comprising a borate buffer.

9. The aqueous suspension agent of claim 1, wherein the aqueous suspension agent has a pH of about 4 to about 8.

* * * * *